(12) United States Patent
Griffith et al.

(10) Patent No.: US 7,659,115 B2
(45) Date of Patent: Feb. 9, 2010

(54) NUCLEIC ACID ENCODING HUMAN TRANSDUCTIN-1 POLYPEPTIDE

(75) Inventors: Andrew Griffith, Rockville, MD (US); Kiyoto Kurima, Gaithersburg, MD (US); Edward Wilcox, Gaithersburg, MD (US); Thomas Friedman, Potomac, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 11/615,250

(22) Filed: Dec. 22, 2006

(65) Prior Publication Data

US 2007/0099271 A1    May 3, 2007

Related U.S. Application Data

(62) Division of application No. 10/487,887, filed as application No. PCT/US02/29614 on Sep. 19, 2002, now Pat. No. 7,192,705.

(60) Provisional application No. 60/323,275, filed on Sep. 19, 2001.

(51) Int. Cl.
*C07H 21/04* (2006.01)
*C12N 15/00* (2006.01)
*C12N 5/00* (2006.01)

(52) U.S. Cl. .................. 435/325; 536/23.1; 536/23.5; 536/24.3; 435/320.1

(58) Field of Classification Search .................. None
See application file for complete search history.

(56) References Cited

U.S. PATENT DOCUMENTS

| 6,040,138 A | 3/2000 | Lockhart et al. |
| 6,197,506 B1 | 3/2001 | Fodor et al. |
| 6,485,908 B1 | 11/2002 | Petit et al. |

FOREIGN PATENT DOCUMENTS

| EP | 1 104 808 A | 6/2001 |
| WO | WO 98/00014 A1 | 1/1998 |
| WO | WO 99/09210 A2 | 2/1999 |
| WO | WO 00/52161 | 9/2000 |
| WO | WO 01/12662 A2 | 2/2001 |
| WO | WO 01/75067 A2 | 10/2001 |
| WO | WO 02/068579 A2 | 9/2002 |

OTHER PUBLICATIONS

Greinwald et al., Genome Res. 7:879-886, 1997.*
Burke et al., Science 4803:806-812; 1987.*
Dang et al., Clin. Cancer Res. 5:471-474, 1999.*
Potter et al., J. Biol. Chem. 233:915-916, 1958.*
Sutcliffe, PNAS 75:3737-3741, 1978.*
Scott et al., Gene 215:461-469, 1998.*
Alagramam et al., The Mouse Ames Waltzer Hearing-Loss Mutant is Caused by Mutation of Pcdh15, A Novel Protocadherin Gene, *Nature Genetics*, 27(1), 99-102 (2001).
Corey et al., "Ionic Basis of the Receptor Potential in a Vertebrate Hair Cell," *Nature*, vol. 281, pp. 675-677 (1979).
Friedman et al., Modifier Genes of Hereditary Hearing Loss, *Current Opinion in Neurobiology*, 10(4), 487-493 (2000).
Hudspeth et al., "Sensitivity, Polarity, and Conductance Change in the Response of Vertebrate Hair Cells to Controlled Mechanical Stimuli," *Proc. Natl. Acad. Sci. USA*, vol. 74 (6), pp. 2407-2411 (1977).
Jain et al., "A Human Recessive Neurosensory Nonsyndromic Hearing Impairment Locus is a Potential Homologue of the Murine Deafness (*dn*) Locus," *Hum. Mol. Genet.*, vol. 4 (12), pp. 2391-2394 (1995).
Kurima, et al., "Dominant and Recessive Deafness Caused by Mutations of a Novel Gene, *TMC1*, Required for Cochlear Hair-Cell Function," *Nat. Genet.*, vol. 30, pp. 277-284 (2002) .
Kurima et al., "Genetic Map Localization of DFNA34 and DFNA36, Two Autosomal Dominant Non-Syndromic Deafness Loci." *Am. J. Hum. Genet.*, vol. 67, p. 300 (2000).
Kurima et al., "Genetic Map Localization of DFNA34 and DFNA36, Two Novel Autosomal Dominant Nonsyndromic Deafness Loci," *ARO Abstracts*, vol. 24, p. 265 (2001).
Scott et al., "Refining the DFNB7-DFNB11 Deafness Locus Using Intragenic Polymorphisms in a Novel Gene, *TMEM2*," *Gene*, vol. 246, pp. 265-274 (2000).
EBI Accession No. AX977361, Jan. 15, 2004.
EBI Accession No. AK016832: Feb. 9, 2001.
EBI Accession No. AAB08764: Jan. 2, 2001.
EBI Accession No. Q9H766: Mar. 1, 2001.
EBI Accession No. AAB74730: Jan. 12, 2001.
EBI Accession No. HS692H20T: Dec. 14, 1998.
EBI Accession No. ABG28109: Feb. 18, 2002.
EBI Accession No. AAS92296: Feb. 13, 2002.

* cited by examiner

*Primary Examiner*—David J Steadman
(74) *Attorney, Agent, or Firm*—Leydig, Voit & Mayer, Ltd.

(57) ABSTRACT

The invention provides isolated or purified nucleic molecules consisting of a nucleotide sequence encoding human transductin-1 (TDC1), such as SEQ ID NO: 1. The invention also provides vectors comprising the isolated or purified nucleic acid sequences and cells comprising such vectors.

8 Claims, 8 Drawing Sheets

```
CAGAAACTATGAGGGCAGAACCCAGCAATCTGTGCTTTCTTTCACAAGCCCTCCAGGAGT   60
TGCTGAAATTTAGGAATCATTGCCCCAAAAAGTGGCCCTCATAATGATGCCAGATGGGAT  120
CTTACTCTGTTGCCCAGGCTGGAGTGCAGTGGTGCGATCTCGGCTCTCTGCAACCTCCGC  180
CTCCCAGGTTCAAGTGATTCTCCTGCCTCGGCCTCCTGAGTAGCTGGGATTTCAGGCCAT  240
GAAAGATCACTGTTTTAGTCTGCGTGGTGCAGTGGAACAGATAGACCTCGGTTTGAATCT  300
CAGCTCTACTGTTTACTAGACGTGAAATGGGGAAATCTAAAATGAGATGCCAGAAGCCTC  360
AAAAATGGAAAACCCCTGTGCTTCACATCTGAAAATCTCTGCTGGGGGCAGCAACTTTG   420
AGCCTGTGGGGAAGGAACTGTCCACGTGGAGTGGTCTGGTGAATGCTTAAGGAGCTGCAG  480
AAGGGAAGTCCCTCTCCAAACTAGCCAGCCACTGAGACCTTCTGACAGGACACCCCCAGG  540
ATGTCACCCAAAAAAGTACAAATCAAAGTGGAGGAAAAAGAAGACGAGACTGAGGAAAGC  600
TCAAGTGAAGAGGAAGAGGAGGTGGAAGATAAGCTACCTCGAAGAGAGAGCTTGAGACCA  660
AGAGGAAACGGACCAGAGATGTTATCAATGAGGATGACCCAGAACCTGAACCAGAGGAT   720
GAAGAAACAAGGAAGGCAAGAGAAAAAGAGAGGAGGAGGAGGCTAAAGAGAGGAGCAGAA  780
AAAGAAGAAATTGATGAAGAGGAATTGGAAAGATTGAAGGCAGAGTTAGATGAGAAAAGA  840
CAAATAATTGCTACTGTCAAATGCAAACCATGGAAGATGGAGAAGAAAATTGAAGTTCTC  900
AAGGAGGCAAAAAAATTTGTGAGTGAAAATGAAGGGGCTCTTGGGAAAGGAAAAGGAAAA  960
CGGTGGTTTGCATTTAAGATGATGATGGCCAAGAAATGGGCAAAATTCCTCCGTGATTTT 1020
GAGAACTTCAAAGCTGCGTGTGTCCCATGGGAAAATAAAATCAAGGCTATTGAAAGTCAG 1080
TTTGGCTCCTCAGTGGCCTCATACTTCCTCTTCTTGAGATGGATGTATGGAGTCAATATG 1140
GTTCTCTTTATCCTGACATTTAGCCTCATCATGTTGCCAGAGTACCTCTGGGGTTTGCCA 1200
TATGGCAGTTTACCTAGGAAAACCGTTCCCAGAGCCGAAGAGGCATCGGCAGCAAACTTT 1260
GGTGTGTTGTACGACTTCAATGGTTTGGCACAATATTCCGTTCTCTTTTATGGCTATTAT 1320
GACAATAAACGAACAATTGGATGGATGAATTTCAGGTTGCCGCTCTCCTATTTTCTAGTG 1380
GGGATTATGTGCATTGGATACAGCTTTCTGGTTGTCCTCAAAGCAATGACCAAAAACATT 1440
GGTGATGATGGAGGTGGAGATGACAACACTTTCAATTTCAGCTGGAAGGTCTTTACCAGC 1500
TGGGACTACCTGATCGGCAATCCTGAAACAGCAGACAACAAATTTAATTCTATCACAATG 1560
AACTTTAAGGAAGCTATCACAGAAGAAAAGCAGCCCAAGTAGAAGAAAACGTCCACTTG   1620
ATCAGATTCCTGAGGTTTCTGGCTAACTTCTTCGTGTTTCTAACACTTGGAGGGAGTGGA 1680
TACCTCATCTTTTGGGCTGTGAAGCGATCCCAGGAATTTGCACAGCAAGATCCTGACACC 1740
CTTGGGTGGTGGGAAAAAAATGAAATGAACATGGTTATGTCCCTCCTAGGGATGTTCTGT 1800
CCAACATTGTTTGACTTATTTGCTGAATTAGAAGACTACCATCCTCTCATCGCTTTGAAA 1860
TGGCTACTGGGACGCATTTTTGCTCTTCTTTTAGGCAATTTATACGTATTTATTCTTGCA 1920
TTAATGGATGAGATTAACAACAAGATTGAAGAGGAGAAGCTAGTAAAGGCCAATATTACC 1980
CTTTGGGAAGCCAATATGATCAAGGCCTACAATGCATCATTCTCTGAAAATAGCACTGGA 2040
CCACCCTTTTTTGTTCACCCTGCAGATGTACCTCGAGGACCTTGCTGGGAAACAATGGTG 2100
GGACAGGAGTTTGTGAGGCTGACAGTCTCTGATGTTCTGACCACCTACGTCACAATCCTC 2160
ATTGGGGACTTTCTAAGGGCATGTTTTGTGAGGTTTTGCAATTATTGCTGGTGCTGGGAC 2220
TTGGAGTATGGATATCCTTCATACACCGAATTCGACATCAGTGGCAACGTCCTCGCTCTG 2280
ATCTTCAACCAAGGCATGATCTGGATGGGCTCCTTCTTTGCTCCCAGCCTCCCAGGCATC 2340
AATATCCTTCGACTCCATACATCCATGTACTTCCAGTGCTGGGCCGTTATGTGCTGCAAT 2400
GTTCCTGAGGCCAGGGTCTTCAAAGCTTCCAGATCAAATAACTTCTACCTGGGCATGCTA 2460
CTGCTCATCCTCTTCCTGTCCACAATGCCTGTCTTGTACATGATCGTGTCCCTCCCACCA 2520
TCTTTTGATTGTGGTCCATTCAGTGGCAAAAATAGAATGTTTGAAGTCATTGGAGAGACC 2580
CTGGAGCACGATTTCCCAAGCTGGATGGCGAAGATCTTGAGACAGCTTTCAAACCCTGGG 2640
CTGGTCATTGCTGTCATTTGGTGATGGTTTTGGCCATCTATTATCTCAATGCTACTGCC  2700
AAGGGCCAGAAGGCAGCGAATCTGGATCTCAAAAGAAGATGAAAATGCAAGCTTTGGAG  2760
```

FIGURE 1

```
AACAAAATGCGAAACAAGAAAATGGCAGCTGCACGAGCAGCTGCAGCTGCTGGTCGCCAG 2820
TAATAAGTATCCTGAGAGCCCAGAAAAGGTACACTTTGCCTTGCTGTTTAAAAGTAATGC 2880
AATATGTGAACGCCCAGAGAACAAGCACTGTGGAACTGCTATTTTCCTGTTCTACCCTTG 2940
ATGGATTTTCAAGGTCATGCTGGCCAATTAAGGCATCATCAGTCCTACCTGAGCAACAAG 3000
AATCTAAACTTTATTCCAAGTCAGAAACTGTTTCTGCAGAGCCACTCTCTCCCCTGCTCC 3060
ATTTCGTGACTTTTTTTTTTTTTTAACAAATTGAGTTTAGAAGTGAGTGTAATCCAGCA 3120
ATACAGTTTACTGGTTTAGTTGGTGGGTTAATTAAAAAAAATTTGCTCATATGAACTTTC 3180
ATTTTATATGTTTCTTTTGCCTGAGTTTCCTTAAACTGAGAGCAGAAATATTTCACCCTT 3240
TTTCCTCTAAGTTCAGAAATATTTGCAAAAAGTACTCATTGTAATCATTCATTAACTCAC 3300
TTTTTGAAACCAATACCTTATTTTCTCTTTTTTTCTACCTGTCTCCCCAACCACGCGCCC 3360
CACAAATATATTCCTAAAACCTTTGTATTTGGTGCTGGATTCAGTATGAAAAGAAATAGG 3420
GTTTTTAGAAGAAAAAAAAATCCTATATGAATTGGGGCCTGGATAGCACTGAGGTTGAAG 3480
ATCTTGAAGATCTCTTACTTTGAGAAGGTACATGAGTCTTACACAACCTAGCTTTTTATG 3540
AGATAAAATTAAAAAAAAAAGGAAAGACATCATAAATGACTGTTGTTCTCTCACAGTCTG 3600
CTCATTTGTCTTCCAATGATCATGTTATCAGTGGTGAATCCATACAGGTCTGCATCAAAC 3660
TCGATACAATTCTTGCCTCCTTGGAGGGAAGAATTCAGCTGAGGGGCAGAAGTAGGTTTA 3720
TGGCAGAGGGAGAGAATGAGGCAAGTTTTAGAGCAGGAGTGTAGGTTTATTAAAAAGTTT 3780
TACAGCAGGAACAAAAGGAAATAAAATATACTTGGAAGAGAGCCAAGTGGGCAAATTGAG 3840
AGTTCCAAGTGCCCTGTTCAGCTTTGACCTGGGTTTCTATACACTGGCATGGTTCTGGAG 3900
TTTGCATCTCTCCCCGCTTGATTTTTTTGGCGGATGGGCTGTCCGTGTGGATGGTGGCCT 3960
GCCGGCAGTTGGAAGGAGCTATGTGTACAATGTGTTACTGAAGTTGTGTGCCTGCTCACT 4020
TGTGACGTTTTCCCTTACCATCCAGCGTTCCTGGAGGAAGGTCATATACTAGTTAAACTC 4080
TGCCATTTTGCTTAGTGGGCATGCTTGAGCCCACTTGCCCAACTCCTAAGATCTCCGGCT 4140
CAGGTGTTTTCTATCTATTGGGAGACTGTCTTTCCCTAGCACTGGTTGCCACTAATTATT 4200
ATTTTAGAGAGATAGTTTAACCACCACCTGACCATCACCAAATGGTCACCTGACATTCCT 4260
GTGGGATGGGTGGTGGGGGGCCTCTCTTGCCCTGCTTATGTTTTATGTTTGCCTAACTA 4320
CCTACTCTAACAA (SEQ ID NO: 1)                                 4333
```

```
MSPKKVQIKVEEKEDETEESSSEEEEEVEDKLPRRESLRPKRKRTRDVINEDDPEPEPED  60
EETRKAREKERRRRLKRGAEKEEIDEEELERLKAELDEKRQIIATVKCKPWKMEKKIEVL 120
KEAKKFVSENEGALGKGKGKRWFAFKMMMAKKWAKFLRDFENFKAACVPWENKIKAIESQ 180
FGSSVASYFLFLRWMYGVNMVLFILTFSLIMLPEYLWGLPYGSLPRKTVPRAEEASAANF 240
GVLYDFNGLAQYSVLFYGYYDNKRTIGWMNFRLPLSYFLVGIMCIGYSFLVVLKAMTKNI 300
GDDGGGDDNTFNFSWKVFTSWDYLIGNPETADNKFNSITMNFKEAITEEKAAQVEENVHL 360
IRFLRFLANFFVFLTLGGSGYLIFWAVKRSQEFAQQDPDTLGWWEKNEMNMVMSLLGMFC 420
PTLFDLFAELEDYHPLIALKWLLGRIFALLLGNLYVFILALMDEINNKIEEEKLVKANIT 480
LWEANMIKAYNASFSENSTGPPFFVHPADVPRGPCWETMVGQEFVRLTVSDVLTTYVTIL 540
IGDFLRACFVRFCNYCWCWDLEYGYPSYTEFDISGNVLALIFNQGMIWMGSFFAPSLPGI 600
NILRLHTSMYFQCWAVMCCNVPEARVFKASRSNNFYLGMLLLILFLSTMPVLYMIVSLPP 660
SFDCGPFSGKNRMFEVIGETLEHDFPSWMAKILRQLSNPGLVIAVILVMVLAIYYLNATA 720
KGQKAANLDLKKKMKMQALENKMRNKKMAAARAAAAGRQ (SEQ ID NO: 2)       760
```

FIGURE 1 CONT.

```
GCAGTGCTGCTGACCATGAGCCACCAGGTAAAGGGCCTGAAAGAGGAAGGTGACAGGCTG    60
GGAAGGAGATCCTCAAGCAAGCGGGCTCTCAAAGCCGAGGGGACCCCAGGCAGGCGCGGA   120
GCTCAGCGAAGCCAGAAGGAGCGCGCCGGGGGCAGCCCAAGCCCGGGGTCTCCCCGGAGG   180
AAGCAAACAGGGCGCAGGAGACACAGAGAAGAGCTGGGGGAGCAGGAGCGGGGCGAGGCA   240
GAGAGGACCTGCGAGGGCAGGAGAAAGCGCGACGAGAGGGCCTCCTTCCAGGAGCGGACA   300
GCAGCCCCAAAGAGGGAAAAGGAGATTCCGAGGAAGGAGGAGAAGTCGAAGCGGCAGAAG   360
AAACCCAGGTCATCCTCCTTGGCCTCCAGTGCCTCTGGTGGGGAGTCCCTGTCCGAGGAG   420
GAACTGGCCCAGATCCTGGAGCAGGTGGAAGAAAAAAGAAGCTCATTGCCACCATGCGG   480
AGCAAGCCCTGGCCCATGGCGAAGAAGCTGACAGAGCTCAGGGAGGCCCAGGAATTTGTG   540
GAGAAGTATGAAGGTGCCTTGGGAAAGGGGAAAGGCAAGCAACTATATGCCTACAAGATG   600
CTGATGGCCAAGAAATGGGTCAAATTTAAGAGAGACTTTGATAATTTCAAGACTCAATGT   660
ATCCCCTGGGAAATGAAGATCAAGGACATTGAAAGTCACTTTGGTTCTTCAGTGGCATCG   720
TATTTCATCTTTCTCCGATGGATGTATGGAGTTAACCTTGTCCTTTTTGGCTTAATATTT   780
GGTCTAGTCATAATCCCAGAGGTACTGATGGGCATGCCCTATGGGAGTATTCCCAGAAAG   840
ACAGTGCCTCGGGCTGAGGAAGAAAAGGCCATGGATTTTTCTGTCCTTTGGGATTTTGAG   900
GGCTATATCAAGTACTCTGCACTCTTCATGGCTACTACAACAACCAGAGGACCATCGGG   960
TGGCTGAGGTACCGGCTGCCTATGGCTTACTTTATGGTGGGGGTCAGCGTGTTCGGCTAC  1020
AGCCTGATTATTGTCATTCGATCGATGGCCAGCAATACCCAAGGAAGCACAGGCGAAGGG  1080
GAGAGTGACAACTTCACATTCAGCTTCAAGATGTTCACCAGCTGGGACTACCTGATCGGG  1140
AATTCAGAGACAGCTGATAACAAATATGCATCCATCACCACCAGCTTCAAGGAATCAATA  1200
GTGGATGAACAAGAGAGTAACAAAGAAGAAATATCCATCTGACAAGATTTCTTCGTGTC  1260
CTGGCCAACTTTCTCATCATCTGCTGTTTGTGTGGAAGTGGGTACCTCATTTACTTTGTG  1320
GTTAAGCGATCTCAGCAATTCTCCAAAATGCAGAATGTCAGCTGGTATGAAAGGAATGAG  1380
GTAGAGATCGTGATGTCCCTGCTTGGAATGTTTTGTCCCCCTCTGTTTGAAACCATCGCT  1440
GCCCTGGAGAATTACCACCCACGCACTGGACTGAAGTGGCAGCTGGGACGCATCTTTGCA  1500
CTCTTCCTGGGGAACCTCTACACATTTCTCTTGGCCCTGATGGATGACGTCCACCTCAAG  1560
CTTGCTAATGAAGAGACAATAAAGAACATCACTCACTGGACTCTGTTTAACTATTACAAC  1620
TCTTCTGGTTGGAACGAGAGTGTCCCCCGACCACCCCTGCACCCTGCAGATGTGCCCCGG  1680
GGTTCTTGCTGGGAGACAGCTGTGGGCATTGAATTCATGAGGCTGACGGTGTCTGACATG  1740
CTGGTAACGTACATCACCATCCTGCTGGGGGACTTCCTACGGGCTTGTTTTGTGCGGTTC  1800
ATGAACTACTGCTGGTGCTGGGACTTGGAGGCTGGATTTCCTTCATATGCTGAGTTTGAT  1860
ATTAGTGGAAATGTGCTGGGTTTGATCTTCAACCAAGGAATGATCTGGATGGGCTCCTTC  1920
TATGCTCCAGGCCTGGTGGGCATTAATGTGCTGCGCCTGCTGACCTCCATGTACTTCCAG  1980
TGCTGGGCGGTGATGAGCAGCAACGTACCCCATGAACGCGTGTTCAAAGCCTCCCGATCC  2040
AACAACTTCTACATGGGCCTCCTGCTGCTGGTGCTCTTCCTCAGCCTCCTGCCGGTGGCC  2100
TACACCATCATGTCCCTCCCACCCTCCTTTGACTGCGGGCCGTTCAGTGGGAAAACAGA   2160
ATGTACGATGTCCTCCAAGAGACCATTGAAAACGATTTCCCAACCTTCCTGGGCAAGATC  2220
TTTGCTTTCCTCGCCAATCCAGGCCTGATCATCCCAGCCATCCTGCTGATGTTCTTGGCC  2280
ATTTACTACCTGAACTCAGTTTCCAAAAGCCTTTCCCGAGCTAATGCCCAGCTGAGGAAG  2340
AAAATCCAAGTGCTCCGTGAAGTTGAGAAGAGTCACAAATCTGTAAAAGGCAAAGCCACA  2400
GCCAGAGATTCAGAGGACACACCTAAAAGCAGCTCCAAAAATGCCACCCAGCTCCAACTC  2460
ACCAAGGAAGAGACCACTCCTCCCTCTGCCAGCCAAAGCCAGGCCATGGACAAGAAGGCG  2520
CAGGGCCCTGGGACCTCCAATTCTGCCAGCAGGACCACACTGCCTGCCTCTGGACACCTT  2580
CCTATATCTCGGCCCCCTGGAATCGGACCAGATTCTGGCCACGCCCCATCTCAGACTCAT  2640
CCGTGGAGGTCAGCCTCTGGAAAGAGTGCTCAGAGACCTCCCCACTGACGGCTAGGACTC  2700
CAGGGAGCCTCGACCCTAGGGCTGATCCTCAAGTACCCCAGTTTCACACATACCAAACCA  2760
AGGTTCTCTCCCCTCTTTCCTCTCACATACATGCTCTGTCTCCTCTCTTGGAATGCATGA  2820
ACTTTGATTCCTTCAGGCCCTTGTCAGCTACCGAAGGAGGAAGACAGTGGCTTCACCTGT  2880
```

FIGURE 2

```
CCTTTAGGGAAGCTGGAGCCATCTCTGCACTAACTGCCCTCCCAAATATCTTGGTTCAGA  2940
CAGCTCTGAACCCCACGCTCACAGTGGTCGACCTTGCCTCCCGATTTTCGGAGTTGGGGA  3000
AGGGCCATGACCACCCTCGTAGACTTTTTCCATGGGATACAGTTTAGGACACGGGTTTCT  3060
GCCAGCTTCCCTAACCAGGAGGGGGATGGAGAAGGGCCTACATTTCTAATCCAGAGGAA   3120
G (SEQ ID NO: 3)                                              3121

MSHQVKGLKEEGDRLGRRSSSKRALKAEGTPGRRGAQRSQKERAGGSPSPGSPRRKQTGR    60
RRHREELGEQERGEAERTCEGRRKRDERASFQERTAAPKREKEIPRKEEKSKRQKKPRSS   120
SLASSASGGESLSEEELAQILEQVEEKKKLIATMRSKPWPMAKKLTELREAQEFVEKYEG   180
ALGKGKGKQLYAYKMLMAKKWVKFKRDFDNFKTQCIPWEMKIKDIESHFGSSVASYFIFL   240
RWMYGVNLVLFGLIFGLVIIPEVLMGMPYGSIPRKTVPRAEEEKAMDFSVLWDFEGYIKY   300
SALFYGYYNNQRTIGWLRYRLPMAYFMVGVSVFGYSLIIVIRSMASNTQGSTGEGESDNF   360
TFSFKMFTSWDYLIGNSETADNKYASITTSFKESIVDEQESNKEENIHLTRFLRVLANFL   420
IICCLCGSGYLIYFVVKRSQQFSKMQNVSWYERNEVEIVMSLLGMFCPPLFETIAALENY   480
HPRTGLKWQLGRIFALFLGNLYTFLLALMDDVHLKLANEETIKNITHWTLFNYYNSSGWN   540
ESVPRPPLHPADVPRGSCWETAVGIEFMRLTVSDMLVTYITILLGDFLRACFVRFMNYCW   600
CWDLEAGFPSYAEFDISGNVLGLIFNQGMIWMGSFYAPGLVGINVLRLLTSMYFQCWAVM   660
SSNVPHERVFKASRSNNFYMGLLLLVLFLSLLPVAYTIMSLPPSFDCGPFSGKNRMYDVL   720
QETIENDFPTFLGKIFAFLANPGLIIPAILLMFLAIYYLNSVSKSLSRANAQLRKKIQVL   780
REVEKSHKSVKGKATARDSEDTPKSSSKNATQLQLTKEETTPPSASQSQAMDKKAQGPGT   840
SNSASRTTLPASGHLPISRPPGIGPDSGHAPSQTHPWRSASGKSAQRPPH            890
(SEQ ID NO: 4)
```

FIGURE 2 CONT.

```
TTGCAATTCCTGATTAGAGACATTCTGGCAGGATACCTTCAGGATGCCACCCAAAAAAGG   60
TGTGTCTGGCCATTTCTGATGCAARGKTGCCTGTCTTCCTCTTARCTCCTGTCCTGGACA  120
TTCATTATCAAGGCACAAGATTACATTCCTCCTCAACTCTTTTATGTTGCAAATCCAAGT  180
GGAGGAGAAAGAAGAGGATACAGAGGAAAGCTCAAGTGAAGAAGAAGAAGATAAGCTACC  240
CAGAAGAGAGAGCTTGAGACCAAAGAGGAAACGGACCAGAGATGTCATCAATGAGGATGA  300
CCCAGAACCGGAGCCGGAGGATGAAGAAACAAGAAAGGCAAGAGAAAAGAAAGGCGGAG   360
GAGGCTGCGGAGAGGAGCGGAAGAAGAAGAAGAAATTGATGAAGAGGAATTAGAACGGTT  420
AAAAGCACTGCTCGATGAGAATAGACAAATGATCGCTACTGTCAAATGTAAACCTTGGAA  480
AATGGAGAAGAAAATTGAAGTTCTCAAGGAAGCAAAGAAATTTGTGAGTGAGAATGAAGG  540
CGCTCTTGGGAAAGGAAAGGGAAAGAAGTGGTTTGCATTTAAGATGATGATGGCCAAGAA  600
ATGGGCAAAATTCCTCCGAGATTTTGAGAACTTCAAAGCGGCTTGCGTCCCATGGGAAAA  660
CAAAATCAAGGCAATTGAAAGTCAGTTTGGTTCCTCAGTGGCCTCGTACTTCCTGTTCCT  720
CAGGTGGATGTACGGCGTCAACATGGTTCTCTTTGTTGACCTTCAGCCTCATCATGTT    780
ACCGGAGTACCTCTGGGGTTTACCGTACGGCAGCTTACCTAGGAAAACAGTCCCAAGAGC  840
TGAAGAAGCATCTGCAGCCAACTTTGGTGTGTTGTATGACTTCAATGGCCTGGCGCAGTA  900
CTCTGTCCTCTTTTATGGCTATTACGACAATAAACGCACGATCGGATGGCTGAATTTCCG  960
GCTACCTCTTTCCTACTTCCTGGTGGGGATTATGTGCATTGGATACAGCTTCCTGGTTGT 1020
CCTCAAAGCGATGACCAAAAATATTGGTGACGATGGTGGTGGCGATGACAACACTTTCAA 1080
CTTCAGCTGGAAGGTGTTCTGTAGCTGGGACTATCTGATTGGTAACCCTGAAACAGCCGA 1140
CAACAAGTTTAACTCTATCACGATGAACTTTAAGGAAGCCATCATAGAAGAGAGCCGC   1200
ACAGGTGGAGGAGAACATCCACCTCATCAGATTTCTGAGGTTTCTCGCTAACTTCTTCGT 1260
GTTCCTCACACTTGGTGCAAGTGGATACCTCATCTTTTGGGCTGTGAAGCGATCCCAGGA 1320
GTTCGCCCAGCAAGATCCTGACACCCTTGGGTGGTGGGAAAAAAATGAAATGAACATGGT 1380
AATGTCCCTCCTGGGGATGTTCTGTCCCACCCTGTTTGACTTATTTGCTGAACTGGAAGA 1440
TTACCATCCTCTCATTGCTCTGAAGTGGCTCCTGGGGCGCATTTTTGCTCTTCTTCTAGG 1500
CAACTTGTATGTATTCATTCTCGCCTTGATGGATGAGATTAACAACAAGATTGAAGAGGA 1560
GAAGCTTGTGAAGGCTAATATTACCCTGTGGGAAGCCAACATGATTAAGGCTTACAATGA 1620
ATCTCTCTCTGGGCTCTCTGGGAACACCACAGGAGCACCCTTTTTCGTTCATCCTGCAGA 1680
TGTCCCTCGCGGTCCCTGCTGGGAAACAATGGTGGGGCAGGAATTCGTGCGTCTCACCGT 1740
TTCTGACGTCCTGACCACTTACGTCACGATCCTCATTGGCGACTTCCTCAGAGCATGTTT 1800
CGTGAGGTTCTGCAATTACTGCTGGTGCTGGACTTAGAATATGGATATCCTTCATACAC  1860
AGAATTCGACATCAGTGGCAACGTCCTCGCTCTGATCTTCAACCAAGGCATGATCTGGAT 1920
GGGCTCCTTCTTCGCTCCTAGCCTCCCGGGCATCAACATCCTCCGTCTCCACACATCCAT 1980
GTATTTCCAGTGCTGGGCTGTGATGTGCTGCAATGTTCCCGAGGCCAGGGTGTTCAAAGC 2040
TTCCAGATCCAACAACTTCTACCTCGGCATGCTGCTACTCATCCTCTTCCTGTCCACCAT 2100
GCCAGTCCTGTACATGATCGTCTCCCTCCCGCCATCTTTTGATTGTGGGCCCTTCAGTGG 2160
TAAAAACAGGATGTTTGAAGTCATCGGTGAGACCCTGGAACATGACTTCCAAGCTGGAT  2220
GGCGAAGATCCTGAGGCAGCTTTCTAACCCCGGCCTTGTCATTGCTGTCATTCTGGTGAT 2280
GGTCCTGACCATCTATTATCTCAATGCTACTGCCAAGGGCCAGAAAGCAGCGAATCTGGA 2340
CCTCAAAAGAAGATGAAACAGCAAGCTTTGGAGAACAAAATGCGAAACAAGAAAATGGC  2400
AGCGGCTCGAGCAGCTGCAGCTGCTGGTGGCCAGTAATTTTATCAAATGTCCTGGAGGTG 2460
CCCAGAAGTACTCTTCACTTCTGTCTTTGTATGGACAGAGTGAGGGCCAGTGAACTGCTG 2520
CTCTATACTCTACCACCAATGCACCATCATGGCYGCAGTCATGACCATCTGKCAAGGAAT 2580
CATCAGCCCTCTTTGARCAARAARAATCTCACCATTATTTATGGGAATTTTTTCAAAGAA 2640
TTCTTGAACTCCTCTTCTTCTCTYTCTCTCCTGGACAAAGKTTCTCAAACAAATGGGAGT 2700
TTAAATGTGGGTGTGATGTAGTGATACAAATTACTGGGTAAAAATGATAGGATACTTTAA 2760
```

FIGURE 3

```
AAAAGTCAACATTTCCTCATATGGACTTTTTCTTACACACTGGTCTAGTTTCTTAAATGA  2820
GAGGAGAGCTATTACAACATCCTTTGCTATCTAAATTTGGAACTATCTGCATGAAGCATT  2880
CCTTGGGATCATTCA   (SEQ ID NO: 5)                              2895

MLQIQVEEKEEDTEESSSEEEEDKLPRRESLRPKRKRTRDVINEDDPEPEPEDEETRKAR   60
EKERRRRLRRGAEEEEEIDEEELERLKALLDENRQMIATVKCKPWKMEKKIEVLKEAKKF   120
VSENEGALGKGKGKKWFAFKMMMAKKWAKFLRDFENFKAACVPWENKIKAIESQFGSSVA   180
SYFLFLRWMYGVNMVLFVLTFSLIMLPEYLWGLPYGSLPRKTVPRAEEASAANFGVLYDF   240
NGLAQYSVLFYGYYDNKRTIGWLNFRLPLSYFLVGIMCIGYSFLVVLKAMTKNIGDDGGG   300
DDNTFNFSWKVFCSWDYLIGNPETADNKFNSITMNFKEAIIEERAAQVEENIHLIRFLRF   360
LANFFVFLTLGASGYLIFWAVKRSQEFAQQDPDTLGWWEKNEMNMVMSLLGMFCPTLFDL   420
FAELEDYHPLIALKWLLGRIFALLLGNLYVFILALMDEINNKIEEEKLVKANITLWEANM   480
IKAYNESLSGLSGNTTGAPFFVHPADVPRGPCWETMVGQEFVRLTVSDVLTTYVTILIGD   540
FLRACFVRFCNYCWCWDLEYGYPSYTEFDISGNVLALIFNQGMIWMGSFFAPSLPGINIL   600
RLHTSMYFQCWAVMCCNVPEARVFKASRSNNFYLGMLLLILFLSTMPVLYMIVSLPPSFD   660
CGPFSGKNRMFEVIGETLEHDFPSWMAKILRQLSNPGLVIAVILVMVLTIYYLNATAKGQ   720
KAANLDLKKKMKQQALENKMRNKKMAAARAAAAGGQ   (SEQ ID NO: 6)          757
```

FIGURE 3 CONT.

```
TGCAAGAGTGGCCAAGTTTGCCGGGCGTGGTGGCACACGCCTTTAATCCGAGCACTCGGG   60
AGGCAGAGGAAGGCGAATTTCTGAGTTCAAGGCCAGCCTGGTCTACAAAGTGAGTTCCAG  120
GACAGCCAGGGCTACACAGAGAAACCCTGTCTCCAAAAACCAAAAAAAAAAAAAAAAATA  180
GTGGCCAAGTTTGTTCCAGAGGCCCCTAGTTGCCGTCAGGTTCCAGGAAGAGGCCAGTGA  240
CCATGACAGCAGGAAGTCACCCCAGGCTGGGCAGTATATGAAGACGTGAGCCAGTGTGAG  300
GGCCTTGAAACTCTGGTAACCATGAGCCCCCAGTTAAAGAGCTTGGACGAGGAAGGTGAC  360
AAGTCAGCAAGGAGACCCACAAGGAAACAAACCTCCAGAGCTGCATGTCCCCAAGACGGG  420
CACCGAGCCCAATCTAGCCGGAAGGATCCTGCTAAGGGTAGCCCAAGACCAGGGTCTTCC  480
CGGAAGAAACAGATGGAACATGGAAGCTATCACAAGGGGTTGCAGGGACAGAAACCACGA  540
AGGTGGAGAGGTCTCTACAGGGGAGGAAGAAGGACCGGAGAACTTCCCTTAAGGAGCAG   600
AGAGCATCTCCAAAGAAGGAGAGGGAGGCTCTGAGGAAGGAGGCAGGCAAGCAGCTGAGA  660
AAACCCAGGTCCACTTCCTTGGGCTCCAGTGTCTCTACTGGAGACTCCCTGTCTGAGGAG  720
GAGCTGGCTCAGATCCTGGAACAGGTAGAAGAAAAAAAGAAGCTCATCACTACCGTGAGG  780
AACAAACCCTGGCCCATGGCAAAGAAGCTGAGGGAACTCAGGGAAGCCCAAGCCTTTGTG  840
GAGAAGTATGAAGGAGCCTTGGGGAAAGGCAAGGGCAAACACCTCTACGCCTACAGGATG  900
ATGATGGCTAAGAAATGGGTCAAGTTTAAGAGGGACTTTGATAATTTCAAGACTCAATGT  960
ATTCCCTGGGAAATGAAGATCAAGGACATTGAAAGTCACTTCGGTTCTTCTGTGGCATCT 1020
TACTTCATCTTTCTCCGATGGATGTATGGAGTTAACCTTGTCCTTTTTGGCTTAATATTT 1080
GGTCTAGTCATCATCCCAGAGGTGCTGATGGGCATGCCCTATGGAAGTATACCCAGAAAG 1140
ACGGTGCCTCGAGCTGAGGAAGAGCGAGCCATGGACTTCTCTGTCCTTTGGGATTTTGAG 1200
GGCTACATCAAATATTCTGCTCTCTTCATGGCTACTACAACAACCAGCGGACCATTGGA  1260
TGGCTGAGGTACAGGCTGCCCATGGCTTACTTTATGGTGGGGGTCAGCGTGTTTGGCTAC 1320
AGCTTGATGATCGTCATTAGGTCGATGGCCAGCAATACCCAGGGTAGCACCAGTGAGGGG 1380
GACAGTGACAGCTTCACATTCAGCTTCAAGATGTTCACCAGCTGGGACTACCTCATCGGG 1440
AATTCAGAGACAGCAGACAACAAATATGTCTCCATCACTACCAGCTTCAAGGAGTCTATA 1500
GTGGACGAACAAGAGAGTAACAAAGAAGGGAATATCCACCTGACAAGATTCCTCCGCGTC 1560
CTGGCCAACTTTCTCATTCTCTGCTGTCTGTGTGGAAGCGGGTACCTCATTTACTTTGTG 1620
GTGAAACGGTCCCAGGAGTTCTCCAAAATGCAAAATGTCAGCTGGTATGAAAGGAATGAG 1680
GTGGAGATCGTGATGTCTTTGCTAGGGATGTTTTGTCCCCCTCTGTTTGAAACCATCGCT 1740
GCCTTGGAGAATTATCACCCACGAACTGGGCTGAAGTGGCAGCTGGGCCGCATCTTTGCC 1800
CTCTTCCTGGGAAACCTCTACACGTTTCTCCTGGCCCTCATGGACGATGTCCACCTTAAG 1860
CTTTCTAATGAGGAAAAAATCAAGAACATCACTCACTGGACCCTGTTTAACTATTACAAT 1920
TCCTCAGGTGGGAATGAGAGTGTGCCCCGGCCACCACCACACCCTGCAGATGTGCCCAGA 1980
GGTTCTTGCTGGGAGACAGCTGTGGGCATTGAGTTTATGAGGCTCACCGTGTCTGACATG 2040
CTGGTAACATACCTCACCATCTTGGTCGGAGATTTCCTCCGAGCTTGTTTTGTCCGGTTC 2100
ATGAATCACTGCTGGTGTTGGGACCTCGAGGCTGGTTTTCCCTCATATGCCGAGTTTGAT 2160
ATTAGTGGAAATGTGTTGGGTTTGATCTTCAACCAAGGAATGATCTGGATGGGCTCCTTC 2220
TATGCTCCAGGACTGGTGGGCATCAATGTCCTGCGCCTGTTGACCTCCATGTACTTCCAG 2280
TGCTGGGCAGTGATGAGCAGCAACGTTCCCCACGAACGTGTGTTTAAAGCCTCCAGATCC 2340
AACAACTTCTACATGGGCCTGCTGCTGTTGGTGCTCTTCCTCAGCCTCCTGCCTGTGGCC 2400
TACACCGTCATGTCTCTCCCACCCTCGTTTGACTGTGGCCCCTTCAGTGGGAAAAACAGA 2460
ATGTACGATGTCCTCCATGAGACCATCGAGAACGATTTCCCTAAGTTCCTGGGCAAGATC 2520
TTTGCGTTCCTTGCCAACCCAGGCCTGATCATTCCAGCCATCCTGCTAATGTTTCTGGCC 2580
ATTTACTATCTGAACTCAGTTTCAAAAAGTCTTTCTAGAGCTAATGCCCAGCTGCGAAAG 2640
AAGATCCAAGCGCTCCGTGAAGTTGAGAAGAACCATAAATCCATCAAGGGAAAAGCCATA 2700
GTCACATATTCAGAGGACACAATCAAGAACAGCTCCAAAAATGCCACCCAGATACATCTT 2760
ACTAAAGAAGAGCCCACATCTCACTCTTCCAGCCAAATCCAGACCCTGGACAAGAAAGCG 2820
CAGGGCCCCCACACCTCCAGTACTGAGGGTGGGGCCTCGCCATCTACCTCCTGGCACCAT 2880
GTTGGGTCTCAACCACCGAGAGGCAGACGAGATTCTGGCCAACCCCAGTCTCAGACTTAC 2940
ACAGGCAGGTCACCTTCTGGAAAGAGAACCCAGAGGCCTCACAACTGATTTTCTGGCATT 3000
```

FIGURE 4

```
CATGGGTGTCCCAGTCCTTGGCTTGAATCTCTACTGTTTTATATATCTCTTCCCTTCTCA  3060
TCTCACATATACAAATGTTTCCCTATGGCTTATGTAACATATGAACTTTAATCCTTGCTT  3120
CCAGCCCTTGATTACTACCTAAAGGGAAGAGCAATGGACCTCACACACTAGCGGTTTCCT  3180
TTGGCTCCAGACTTGAGGAGGCAGGGATGAGGCCAT  (SEQ ID NO: 7)           3216

MSPQLKSLDEEGDKSARRPTRKQTSRAACPQDGHRAQSSRKDPAKGSPRPGSSRKKQMEH    60
GSYHKGLQGQKPRKVERSLQGRKKDRRTSLKEQRASPKKEREALRKEAGKQLRKPRSTSL   120
GSSVSTGDSLSEEELAQILEQVEEKKKLITTVRNKPWPMAKKLRELREAQAFVEKYEGAL   180
GKGKGKHLYAYRMMMAKKWVKFKRDFDNFKTQCIPWEMKIKDIESHFGSSVASYFIFLRW   240
MYGVNLVLFGLIFGLVIIPEVLMGMPYGSIPRKTVPRAEEERAMDFSVLWDFEGYIKYSA   300
LFYGYYNNQRTIGWLRYRLPMAYFMVGVSVFGYSLMIVIRSMASNTQGSTSEGDSDSFTF   360
SFKMFTSWDYLIGNSETADNKYVSITTSFKESIVDEQESNKEGNIHLTRFLRVLANFLIL   420
CCLCGSGYLIYFVVKRSQEFSKMQNVSWYERNEVEIVMSLLGMFCPPLFETIAALENYHP   480
RTGLKWQLGRIFALFLGNLYTFLLALMDDVHLKLSNEEKIKNITHWTLFNYYNSSGGNES   540
VPRPPPHPADVPRGSCWETAVGIEFMRLTVSDMLVTYLTILVGDFLRACFVRFMNHCWCW   600
DLEAGFPSYAEFDISGNVLGLIFNQGMIWMGSFYAPGLVGINVLRLLTSMYFQCWAVMSS   660
NVPHERVFKASRSNNFYMGLLLLVLFLSLLPVAYTVMSLPPSFDCGPFSGKNRMYDVLHE   720
TIENDFPKFLGKIFAFLANPGLIIPAILLMFLAIYYLNSVSKSLSRANAQLRKKIQALRE   780
VEKNHKSIKGKAIVTYSEDTIKNSSKNATQIHLTKEEPTSHSSSQIQTLDKKAQGPHTSS   840
TEGGASPSTSWHHVGSQPPRGRRDSGQPQSQTYTGRSPSGKRTQRPHN               888
SEQ ID NO: 8)
```

FIGURE 4 (CONT.)

SEQUENCE LISTING

```
<160> NUMBER OF SEQ ID NOS: 8

<210> SEQ ID NO 1
<211> LENGTH: 4333
<212> TYPE: DNA
<213> ORGANISM: Homo sapiens

<400> SEQUENCE: 1
cagaaactat gagggcagaa cccagcaatc tgtgctttct ttcacaagcc ctccaggagt      60
tgctgaaatt taggaatcat tgccccaaaa agtggccctc ataatgatgc cagatgggat     120
cttactctgt tgcccaggct ggagtgcagt ggtgcgatct cggctctctg caacctccgc     180
ctcccaggtt caagtgattc tcctgcctcg gcctcctgag tagctgggat tcaggccat     240 gaaagatcac tgttttagtc tgcgtggtgc agtggaacag atagacctcg gtttgaatct     300
cagctctact gtttactaga cgtgaaatgg ggaaatctaa aatgagatgc cagaagcctc     360
aaaaatggaa aaccccctgt gcttcacatc tgaaaatctc tgctggggc agcaactttg      420 agcctgtggg gaaggaactg tccacgtgga gtggtctggt gaatgcttaa ggagctgcag     480
aagggaagtc cctctccaaa ctagccagcc actgagacct tctgacagga cacccccagg     540
atgtcaccca aaaaagtaca aatcaaagtg gaggaaaaag aagacgagac tgaggaaagc     600
tcaagtgaag aggaagagga ggtggaagat aagctacctc gaagagagag cttgagacca     660
aagaggaaac ggaccagaga tgttatcaat gaggatgacc cagaacctga accagaggat     720
gaagaaacaa ggaaggcaag agaaaaagag aggaggagga ggctaaagag aggagcagaa     780
aaagaagaaa ttgatgaaga ggaattggaa agattgaagg cagagttaga tgagaaaaga     840
caaataattg ctactgtcaa atgcaaacca tggaagatgg agaagaaaat tgaagttctc     900
```

```
aaggaggcaa aaaaatttgt gagtgaaaat gaagggctc ttgggaaagg aaaaggaaaa      960
cggtggtttg catttaagat gatgatggcc aagaaatggg caaaattcct ccgtgatttt     1020
gagaacttca aagctgcgtg tgtcccatgg gaaaataaaa tcaaggctat tgaaagtcag     1080
tttggctcct cagtggcctc atacttcctc ttcttgagat ggatgtatgg agtcaatatg     1140
gttctcttta tcctgacatt tagcctcatc atgttgccag agtacctctg ggtttgcca      1200 tatggcagtt tacctaggaa aaccgttccc agagccgaag aggcatcggc agcaaacttt     1260
ggtgtgttgt acgacttcaa tggtttggca caatattccg ttctctttta tggctattat     1320
gacaataaac gaacaattgg atggatgaat ttcaggttgc cgctctccta ttttctagtg     1380
gggattatgt gcattggata cagctttctg gttgtcctca aagcaatgac caaaaacatt     1440
ggtgatgatg gaggtggaga tgacaacact ttcaatttca gctggaaggt ctttaccagc     1500
tgggactacc tgatcggcaa tcctgaaaca gcagacaaca aatttaattc tatcacaatg     1560
aactttaagg aagctatcac agaagaaaaa gcagcccaag tagaagaaaa cgtccacttg     1620
atcagattcc tgaggtttct ggctaacttc ttcgtgtttc taacacttgg agggagtgga     1680
tacctcatct ttggggctgt gaagcgatcc caggaatttg cacagcaaga tcctgacacc     1740
cttgggtggt gggaaaaaaa tgaaatgaac atggttatgt ccctcctagg gatgttctgt     1800
ccaacattgt ttgacttatt tgctgaatta aagactacc atcctctcat cgctttgaaa      1860
tggctactgg gacgcatttt tgctcttctt ttaggcaatt tatacgtatt tattcttgca     1920
ttaatggatg agattaacaa caagattgaa gaggagaagc tagtaaaggc caatattacc     1980
ctttgggaag ccaatatgat caaggcctac aatgcatcat tctctgaaaa tagcactgga     2040
ccaccctttt tgttcaccc tgcagatgta cctcgaggac cttgctggga aacaatggtg      2100
ggacaggagt ttgtgaggct gacagtctct gatgttctga ccacctacgt cacaatcctc     2160 attgggggact tctaaggc atgttttgtg aggttttgca attattgctg gtgctgggac      2220
ttggagtatg gatatccttc atacaccgaa ttcgacatca gtggcaacgt cctcgctctg     2280
atcttcaacc aaggcatgat ctggatgggc tccttctttg ctcccagcct cccaggcatc     2340
aatatccttc gactccatac atccatgtac ttccagtgct gggccgttat gtgctgcaat     2400
gttcctgagg ccagggtctt caaagcttcc agatcaaata acttctacct gggcatgcta     2460
ctgctcatcc tcttcctgtc cacaatgcct gtcttgtaca tgatcgtgtc cctcccacca     2520
tcttttgatt gtggtccatt cagtggcaaa aatagaatgt ttgaagtcat tggagagacc     2580
ctggagcacg atttcccaag ctggatggcg aagatcttga cacagctttc aaaccctggg     2640
ctggtcattg ctgtcatttt ggtgatggtt ttggccatct attatctcaa tgctactgcc     2700
aagggccaga aggcagcgaa tctggatctc aaaaagaaga tgaaaatgca agctttggag     2760
aacaaaatgc gaaacaagaa aatggcagct gcacgagcag ctgcagctgc tggtcgccag     2820
taataagtat cctgagagcc cagaaaaggt acactttgcc ttgctgtttta aaagtaatgc    2880 aatatgtgaa cgcccagaga acaagcactg tggaactgct attttcctgt tctacccttg     2940
atggattttc aaggtcatgc tggccaatta aggcatcatc agtcctacct gagcaacaag     3000
aatctaaact ttattccaag tcagaaactg tttctgcaga gccactctct cccctgctcc     3060
atttcgtgac ttttttttt tttttaacaa attgagttta gaagtgagtg taatccagca     3120
atacagttta ctggtttagt tggtgggtta attaaaaaaa atttgctcat atgaactttc     3180 atttatatg tttcttttgc ctgagtttcc ttaaactgag agcagaaata tttcacccctt    3240 tttcctctaa gttcagaaat atttgcaaaa agtactcatt gtaatcattc attaactcac     3300
```

```
ttttttgaaac caatacctta ttttctcttt ttttctacct gtctccccaa ccacgcgccc    3360
cacaaatata ttcctaaaac ctttgtattt ggtgctggat tcagtatgaa aagaaatagg    3420 gttttagaa gaaaaaaaa tcctatatga attggggcct ggatagcact gaggttgaag     3480
atcttgaaga tctcttactt tgagaaggta catgagtctt acacaaccta gcttttatg    3540 agataaaatt aaaaaaaaaa ggaaagacat cataaatgac tgttgttctc tcacagtctg   3600
ctcatttgtc ttccaatgat catgttatca gtggtgaatc catacaggtc tgcatcaaac   3660
tcgatacaat tcttgcctcc ttggagggaa gaattcagct gaggggcaga agtaggttta   3720
tggcagaggg agagaatgag gcaagttta gagcaggagt gtaggtttat taaaaagttt   3780
tacagcagga acaaaggaa ataaaatata cttggaagag agccaagtgg gcaaattgag    3840
agttccaagt gccctgttca gctttgacct gggtttctat acactggcat ggttctggag   3900
tttgcatctc tccccgcttg attttttgg cggatgggct gtccgtgtgg atggtggcct    3960
gccggcagtt ggaaggagct atgtgtacaa tgtgttactg aagttgtgtg cctgctcact   4020
tgtgacgttt tccttacca tccagcgttc ctggaggaag gtcatatact agttaaactc    4080
tgccattttg cttagtgggc atgcttgagc ccacttgccc aactcctaag atctccggct   4140
caggtgtttt ctatctattg ggagactgtc tttccctagc actggttgcc actaattatt   4200
attttagaga gatagtttaa ccaccacctg accatcacca aatggtcacc tgacattcct   4260
gtgggatggg tggtgggggg cctctcttgc cctgcttatg ttttatgtt tgcctaacta    4320 cctactctaa caa                                                       4333

<210> SEQ ID NO 2
<211> LENGTH: 760
<212> TYPE: PRT
<213> ORGANISM: Homo sapiens

<400> SEQUENCE: 2

Met Ser Pro Lys Lys Val Gln Ile Lys Val Glu Glu Lys Glu Asp Glu
1               5                   10                  15

Thr Glu Glu Ser Ser Glu Glu Glu Glu Val Glu Asp Lys Leu
            20                  25                  30

Pro Arg Arg Glu Ser Leu Arg Pro Lys Arg Lys Arg Thr Arg Asp Val
        35                  40                  45

Ile Asn Glu Asp Asp Pro Glu Pro Glu Pro Glu Asp Glu Glu Thr Arg
    50                  55                  60

Lys Ala Arg Glu Lys Glu Arg Arg Arg Leu Lys Arg Gly Ala Glu
65                  70                  75                  80

Lys Glu Glu Ile Asp Glu Glu Leu Glu Arg Leu Lys Ala Glu Leu
                85                  90                  95

Asp Glu Lys Arg Gln Ile Ile Ala Thr Val Lys Cys Lys Pro Trp Lys
            100                 105                 110

Met Glu Lys Lys Ile Glu Val Leu Lys Glu Ala Lys Lys Phe Val Ser
        115                 120                 125

Glu Asn Glu Gly Ala Leu Gly Lys Gly Lys Gly Lys Arg Trp Phe Ala
    130                 135                 140

Phe Lys Met Met Met Ala Lys Lys Trp Ala Lys Phe Leu Arg Asp Phe
145                 150                 155                 160

Glu Asn Phe Lys Ala Ala Cys Val Pro Trp Glu Asn Lys Ile Lys Ala
                165                 170                 175

Ile Glu Ser Gln Phe Gly Ser Ser Val Ala Ser Tyr Phe Leu Phe Leu
            180                 185                 190
```

-continued

```
Arg Trp Met Tyr Gly Val Asn Met Val Leu Phe Ile Leu Thr Phe Ser
        195                 200                 205

Leu Ile Met Leu Pro Glu Tyr Leu Trp Gly Leu Pro Tyr Gly Ser Leu
    210                 215                 220

Pro Arg Lys Thr Val Pro Arg Ala Glu Glu Ala Ser Ala Ala Asn Phe
225                 230                 235                 240

Gly Val Leu Tyr Asp Phe Asn Gly Leu Ala Gln Tyr Ser Val Leu Phe
                245                 250                 255

Tyr Gly Tyr Tyr Asp Asn Lys Arg Thr Ile Gly Trp Met Asn Phe Arg
            260                 265                 270

Leu Pro Leu Ser Tyr Phe Leu Val Gly Ile Met Cys Ile Gly Tyr Ser
        275                 280                 285

Phe Leu Val Val Leu Lys Ala Met Thr Lys Asn Ile Gly Asp Asp Gly
    290                 295                 300

Gly Gly Asp Asp Asn Thr Phe Asn Phe Ser Trp Lys Val Phe Thr Ser
305                 310                 315                 320

Trp Asp Tyr Leu Ile Gly Asn Pro Glu Thr Ala Asp Asn Lys Phe Asn
                325                 330                 335

Ser Ile Thr Met Asn Phe Lys Glu Ala Ile Thr Glu Glu Lys Ala Ala
            340                 345                 350

Gln Val Glu Glu Asn Val His Leu Ile Arg Phe Leu Arg Phe Leu Ala
        355                 360                 365

Asn Phe Phe Val Phe Leu Thr Leu Gly Gly Ser Gly Tyr Leu Ile Phe
    370                 375                 380

Trp Ala Val Lys Arg Ser Gln Glu Phe Ala Gln Gln Asp Pro Asp Thr
385                 390                 395                 400

Leu Gly Trp Trp Glu Lys Asn Glu Met Asn Met Val Met Ser Leu Leu
                405                 410                 415

Gly Met Phe Cys Pro Thr Leu Phe Asp Leu Phe Ala Glu Leu Glu Asp
            420                 425                 430

Tyr His Pro Leu Ile Ala Leu Lys Trp Leu Leu Gly Arg Ile Phe Ala
        435                 440                 445

Leu Leu Leu Gly Asn Leu Tyr Val Phe Ile Leu Ala Leu Met Asp Glu
    450                 455                 460

Ile Asn Asn Lys Ile Glu Glu Lys Leu Val Lys Ala Asn Ile Thr
465                 470                 475                 480

Leu Trp Glu Ala Asn Met Ile Lys Ala Tyr Asn Ala Ser Phe Ser Glu
                485                 490                 495

Asn Ser Thr Gly Pro Pro Phe Phe Val His Pro Ala Asp Val Pro Arg
            500                 505                 510

Gly Pro Cys Trp Glu Thr Met Val Gly Gln Glu Phe Val Arg Leu Thr
        515                 520                 525

Val Ser Asp Val Leu Thr Thr Tyr Val Thr Ile Leu Ile Gly Asp Phe
    530                 535                 540

Leu Arg Ala Cys Phe Val Arg Phe Cys Asn Tyr Cys Trp Cys Trp Asp
545                 550                 555                 560

Leu Glu Tyr Gly Tyr Pro Ser Tyr Thr Glu Phe Asp Ile Ser Gly Asn
                565                 570                 575

Val Leu Ala Leu Ile Phe Asn Gln Gly Met Ile Trp Met Gly Ser Phe
            580                 585                 590

Phe Ala Pro Ser Leu Pro Gly Ile Asn Ile Leu Arg Leu His Thr Ser
        595                 600                 605
```

```
Met Tyr Phe Gln Cys Trp Ala Val Met Cys Cys Asn Val Pro Glu Ala
        610                 615                 620
Arg Val Phe Lys Ala Ser Arg Ser Asn Asn Phe Tyr Leu Gly Met Leu
625                 630                 635                 640
Leu Leu Ile Leu Phe Leu Ser Thr Met Pro Val Leu Tyr Met Ile Val
            645                 650                 655
Ser Leu Pro Pro Ser Phe Asp Cys Gly Pro Phe Ser Gly Lys Asn Arg
        660                 665                 670
Met Phe Glu Val Ile Gly Glu Thr Leu Glu His Asp Phe Pro Ser Trp
    675                 680                 685
Met Ala Lys Ile Leu Arg Gln Leu Ser Asn Pro Gly Leu Val Ile Ala
690                 695                 700
Val Ile Leu Val Met Val Leu Ala Ile Tyr Tyr Leu Asn Ala Thr Ala
705                 710                 715                 720
Lys Gly Gln Lys Ala Ala Asn Leu Asp Leu Lys Lys Lys Met Lys Met
                725                 730                 735
Gln Ala Leu Glu Asn Lys Met Arg Asn Lys Lys Met Ala Ala Ala Arg
            740                 745                 750
Ala Ala Ala Ala Ala Gly Arg Gln
        755                 760

<210> SEQ ID NO 3
<211> LENGTH: 3121
<212> TYPE: DNA
<213> ORGANISM: Homo sapiens

<400> SEQUENCE: 3
gcagtgctgc tgaccatgag ccaccaggta aagggcctga agaggaagg tgacaggctg      60 ggaaggagat cctcaagcaa gcgggctctc aaagccgagg ggaccccagg caggcgcgga     120
gctcagcgaa gccagaagga gcgcgccggg ggcagcccaa gcccgggtc tccccggagg     180 aagcaaacag ggcgcaggag acacagagaa gagctggggg agcaggagcg gggcgaggca     240
gagaggacct gcgagggcag gagaaagcgc gacgagaggg cctccttcca ggagcggaca     300
gcagccccaa gagggaaaa ggagattccg aggaaggagg agaagtcgaa gcggcagaag     360
aaacccaggt catcctcctt ggcctccagt gcctctggtg gggagtccct gtccgaggag     420
gaactggccc agatcctgga gcaggtgaa gaaaaaaaga agctcattgc caccatgcgg     480
agcaagccct ggcccatggc gaagaagctg acagagctca gggaggccca ggaatttgtg     540
gagaagtatg aaggtgcctt gggaaagggg aaaggcaagc aactatatgc ctacaagatg     600
ctgatggcca agaaatgggt caaatttaag agagactttg ataatttcaa gactcaatgt     660
atcccctggg aaatgaagat caaggacatt gaaagtcact ttggttcttc agtggcatcg     720
tatttcatct ttctccgatg gatgtatgga gttaaccttg tccttttttgg cttaatattt     780 ggtctagtca taatcccaga ggtactgatg gcatgccct atgggagtat cccagaaag     840 acagtgcctc gggctgagga agaaaaggcc atggattttt ctgtcctttg ggattttgag     900
ggctatatca agtactctgc actcttctat ggctactaca caaccagag gaccatcggg     960 tggctgaggt accggctgcc tatggcttac tttatggtgg gggtcagcgt gttcggctac    1020
agcctgatta ttgtcattcg atcgatggcc agcaataccc aaggaagcac aggcgaaggg    1080
gagagtgaca acttcacatt cagcttcaag atgttcacca gctgggacta cctgatcggg    1140
aattcagaga cagctgataa caaatatgca tccatcacca ccagcttcaa ggaatcaata    1200
gtggatgaac aagagagtaa caagaagaa aatatccatc tgacaagatt tcttcgtgtc    1260
```

-continued

```
ctggccaact ttctcatcat ctgctgtttg tgtggaagtg ggtacctcat ttactttgtg    1320
gttaagcgat ctcagcaatt ctccaaaatg cagaatgtca gctggtatga aggaatgag    1380 gtagagatcg tgatgtccct gcttggaatg ttttgtcccc ctctgtttga aaccatcgct    1440
gccctggaga attaccaccc acgcactgga ctgagtggc agctgggacg catctttgca    1500
ctcttcctgg ggaacctcta cacatttctc ttggccctga tggatgacgt ccacctcaag    1560
cttgctaatg aagagacaat aaagaacatc actcactgga ctctgtttaa ctattacaac    1620
tcttctggtt ggaacgagag tgtcccccga ccacccctgc accctgcaga tgtgccccgg    1680
ggttcttgct gggagacagc tgtgggcatt gaattcatga ggctgacggt gtctgacatg    1740
ctggtaacgt acatcaccat cctgctgggg gacttcctac gggcttgttt tgtgcggttc    1800
atgaactact gctggtgctg ggacttggag gctggatttc cttcatatgc tgagtttgat    1860
attagtggaa atgtgctggg tttgatcttc aaccaaggaa tgatctggat gggctccttc    1920
tatgctccag gcctggtggg cattaatgtg ctgcgcctgc tgacctccat gtacttccag    1980
tgctgggcgg tgatgagcag caacgtaccc catgaacgcg tgttcaaagc ctcccgatcc    2040
aacaacttct acatgggcct cctgctgctg gtgctcttcc tcagcctcct gccggtggcc    2100
tacaccatca tgtccctccc accctccttt gactgcgggc cgttcagtgg aaaaacagaa    2160
atgtacgatg tcctccaaga gaccattgaa aacgatttcc caaccttcct gggcaagatc    2220
tttgctttcc tcgccaatcc aggcctgatc atcccagcca tcctgctgat gttcttggcc    2280
atttactacc tgaactcagt ttccaaaagc ctttcccgag ctaatgccca gctgaggaag    2340
aaaatccaag tgctccgtga agttgagaag agtcacaaat ctgtaaaagg caaagccaca    2400
gccagagatt cagaggacac acctaaaagc agctccaaaa atgccaccca gctccaactc    2460
accaaggaag agaccactcc tccctctgcc agccaaagcc aggccatgga caagaaggcg    2520
cagggccctg ggacctccaa ttctgccagc aggaccacac tgcctgcctc tggacacctt    2580
cctatatctc ggccccctgg aatcggacca gattctggcc acgccccatc tcagactcat    2640
ccgtggaggt cagcctctgg aaagagtgct cagagacctc cccactgacg gctaggactc    2700
cagggagcct cgaccctagg gctgatcctc aagtacccca gtttcacaca taccaaacca    2760
aggttctctc ccctctttcc tctcacatac atgctctgtc tcctctcttg gaatgcatga    2820
actttgattc cttcaggccc ttgtcagcta ccgaaggagg aagacagtgg cttcacctgt    2880
cctttaggga agctggagcc atctctgcac taactgccct cccaaatatc ttggttcaga    2940
cagctctgaa ccccacgctc acagtggtcg accttgcctc ccgattttcg gagttgggga    3000
agggccatga ccaccctcgt agactttttc catgggatac agtttaggac acgggttctt    3060
gccagcttcc ctaaccagga gggggatgga gaagggccta catttctcaa tccagaggaa    3120
g                                                                    3121
```

<210> SEQ ID NO 4
<211> LENGTH: 890
<212> TYPE: PRT
<213> ORGANISM: Homo sapiens

<400> SEQUENCE: 4

```
Met Ser His Gln Val Lys Gly Leu Lys Glu Glu Gly Asp Arg Leu Gly
1               5                   10                  15

Arg Arg Ser Ser Ser Lys Arg Ala Leu Lys Ala Glu Gly Thr Pro Gly
            20                  25                  30
```

-continued

```
Arg Arg Gly Ala Gln Arg Ser Gln Lys Glu Arg Ala Gly Gly Ser Pro
        35                  40                  45
Ser Pro Gly Ser Pro Arg Arg Lys Gln Thr Gly Arg Arg His Arg
    50                  55                  60
Glu Glu Leu Gly Glu Gln Glu Arg Gly Glu Ala Glu Arg Thr Cys Glu
65                  70                  75                  80
Gly Arg Arg Lys Arg Asp Glu Arg Ala Ser Phe Gln Glu Arg Thr Ala
                85                  90                  95
Ala Pro Lys Arg Glu Lys Glu Ile Pro Arg Lys Glu Glu Lys Ser Lys
                100                 105                 110
Arg Gln Lys Lys Pro Arg Ser Ser Leu Ala Ser Ser Ala Ser Gly
            115                 120                 125
Gly Glu Ser Leu Ser Glu Glu Leu Ala Gln Ile Leu Glu Gln Val
    130                 135                 140
Glu Glu Lys Lys Lys Leu Ile Ala Thr Met Arg Ser Lys Pro Trp Pro
145                 150                 155                 160
Met Ala Lys Lys Leu Thr Glu Leu Arg Glu Ala Gln Glu Phe Val Glu
                165                 170                 175
Lys Tyr Glu Gly Ala Leu Gly Lys Gly Lys Gly Lys Gln Leu Tyr Ala
                180                 185                 190
Tyr Lys Met Leu Met Ala Lys Lys Trp Val Lys Phe Lys Arg Asp Phe
            195                 200                 205
Asp Asn Phe Lys Thr Gln Cys Ile Pro Trp Glu Met Lys Ile Lys Asp
    210                 215                 220
Ile Glu Ser His Phe Gly Ser Ser Val Ala Ser Tyr Phe Ile Phe Leu
225                 230                 235                 240
Arg Trp Met Tyr Gly Val Asn Leu Val Leu Phe Gly Leu Ile Phe Gly
                245                 250                 255
Leu Val Ile Ile Pro Glu Val Leu Met Gly Met Pro Tyr Gly Ser Ile
                260                 265                 270
Pro Arg Lys Thr Val Pro Arg Ala Glu Glu Lys Ala Met Asp Phe
            275                 280                 285
Ser Val Leu Trp Asp Phe Glu Gly Tyr Ile Lys Tyr Ser Ala Leu Phe
    290                 295                 300
Tyr Gly Tyr Tyr Asn Asn Gln Arg Thr Ile Gly Trp Leu Arg Tyr Arg
305                 310                 315                 320
Leu Pro Met Ala Tyr Phe Met Val Gly Val Ser Val Phe Gly Tyr Ser
                325                 330                 335
Leu Ile Ile Val Ile Arg Ser Met Ala Ser Asn Thr Gln Gly Ser Thr
            340                 345                 350
Gly Glu Gly Glu Ser Asp Asn Phe Thr Phe Ser Phe Lys Met Phe Thr
    355                 360                 365
Ser Trp Asp Tyr Leu Ile Gly Asn Ser Glu Thr Ala Asp Asn Lys Tyr
    370                 375                 380
Ala Ser Ile Thr Thr Ser Phe Lys Glu Ser Ile Val Asp Glu Gln Glu
385                 390                 395                 400
Ser Asn Lys Glu Glu Asn Ile His Leu Thr Arg Phe Leu Arg Val Leu
                405                 410                 415
Ala Asn Phe Leu Ile Ile Cys Cys Leu Cys Gly Ser Gly Tyr Leu Ile
            420                 425                 430
Tyr Phe Val Val Lys Arg Ser Gln Gln Phe Ser Lys Met Gln Asn Val
            435                 440                 445
```

```
Ser Trp Tyr Glu Arg Asn Glu Val Glu Ile Val Met Ser Leu Leu Gly
450                 455                 460

Met Phe Cys Pro Pro Leu Phe Glu Thr Ile Ala Ala Leu Glu Asn Tyr
465                 470                 475                 480

His Pro Arg Thr Gly Leu Lys Trp Gln Leu Gly Arg Ile Phe Ala Leu
                485                 490                 495

Phe Leu Gly Asn Leu Tyr Thr Phe Leu Leu Ala Leu Met Asp Asp Val
            500                 505                 510

His Leu Lys Leu Ala Asn Glu Glu Thr Ile Lys Asn Ile Thr His Trp
        515                 520                 525

Thr Leu Phe Asn Tyr Tyr Asn Ser Ser Gly Trp Asn Glu Ser Val Pro
    530                 535                 540

Arg Pro Pro Leu His Pro Ala Asp Val Pro Arg Gly Ser Cys Trp Glu
545                 550                 555                 560

Thr Ala Val Gly Ile Glu Phe Met Arg Leu Thr Val Ser Asp Met Leu
                565                 570                 575

Val Thr Tyr Ile Thr Ile Leu Leu Gly Asp Phe Leu Arg Ala Cys Phe
            580                 585                 590

Val Arg Phe Met Asn Tyr Cys Trp Cys Trp Asp Leu Glu Ala Gly Phe
        595                 600                 605

Pro Ser Tyr Ala Glu Phe Asp Ile Ser Gly Asn Val Leu Gly Leu Ile
    610                 615                 620

Phe Asn Gln Gly Met Ile Trp Met Gly Ser Phe Tyr Ala Pro Gly Leu
625                 630                 635                 640

Val Gly Ile Asn Val Leu Arg Leu Leu Thr Ser Met Tyr Phe Gln Cys
                645                 650                 655

Trp Ala Val Met Ser Ser Asn Val Pro His Glu Arg Val Phe Lys Ala
            660                 665                 670

Ser Arg Ser Asn Asn Phe Tyr Met Gly Leu Leu Leu Leu Val Leu Phe
        675                 680                 685

Leu Ser Leu Leu Pro Val Ala Tyr Thr Ile Met Ser Leu Pro Pro Ser
    690                 695                 700

Phe Asp Cys Gly Pro Phe Ser Gly Lys Asn Arg Met Tyr Asp Val Leu
705                 710                 715                 720

Gln Glu Thr Ile Glu Asn Asp Phe Pro Thr Phe Leu Gly Lys Ile Phe
                725                 730                 735

Ala Phe Leu Ala Asn Pro Gly Leu Ile Ile Pro Ala Ile Leu Leu Met
            740                 745                 750

Phe Leu Ala Ile Tyr Tyr Leu Asn Ser Val Ser Lys Ser Leu Ser Arg
        755                 760                 765

Ala Asn Ala Gln Leu Arg Lys Lys Ile Gln Val Leu Arg Glu Val Glu
    770                 775                 780

Lys Ser His Lys Ser Val Lys Gly Lys Ala Thr Ala Arg Asp Ser Glu
785                 790                 795                 800

Asp Thr Pro Lys Ser Ser Lys Asn Ala Thr Gln Leu Gln Leu Thr
                805                 810                 815

Lys Glu Glu Thr Thr Pro Pro Ser Ala Ser Gln Ser Gln Ala Met Asp
            820                 825                 830

Lys Lys Ala Gln Gly Pro Gly Thr Ser Asn Ser Ala Ser Arg Thr Thr
        835                 840                 845

Leu Pro Ala Ser Gly His Leu Pro Ile Ser Arg Pro Pro Gly Ile Gly
    850                 855                 860
```

-continued

```
Pro Asp Ser Gly His Ala Pro Ser Gln Thr His Pro Trp Arg Ser Ala
865                 870                 875                 880

Ser Gly Lys Ser Ala Gln Arg Pro Pro His
                885                 890

<210> SEQ ID NO 5
<211> LENGTH: 2895
<212> TYPE: DNA
<213> ORGANISM: Mus musculus

<400> SEQUENCE: 5
ttgcaattcc tgattagaga cattctggca ggataccttc aggatgccac ccaaaaaagg      60
tgtgtctggc catttctgat gcaargktgc ctgtcttcct cttarctcct gtcctggaca     120
ttcattatca aggcacaaga ttacattcct cctcaactct tttatgttgc aaatccaagt     180
ggaggagaaa gaagaggata cagaggaaag ctcaagtgaa gaagaagaag ataagctacc     240
cagaagagag agcttgagac caaagaggaa acggaccaga gatgtcatca atgaggatga     300
cccagaaccg gagccggagg atgaagaaac aagaaaggca agagaaaaag aaaggcggag     360
gaggctgcgg agaggagcgg aagaagaaga gaaaattgat gaagaggaat tagaacggtt     420
aaaagcactg ctcgatgaga atagacaaat gatcgctact gtcaaatgta aaccttggaa     480
aatggagaag aaaattgaag ttctcaagga agcaaagaaa tttgtgagtg agaatgaagg     540
cgctcttggg aaaggaaagg gaaagaagtg gtttgcattt aagatgatga tggccaagaa     600
atgggcaaaa ttcctccgag attttgagaa cttcaaagcg gcttgcgtcc catgggaaaa     660
caaaatcaag gcaattgaaa gtcagtttgg ttcctcagtg gcctcgtact tcctgttcct     720
caggtggatg tacggcgtca acatggttct ctttgtgttg accttcagcc tcatcatgtt     780
accggagtac ctctggggtt taccgtacgg cagcttacct aggaaaacag tcccaagagc     840
tgaagaagca tctgcagcca actttggtgt gttgtatgac ttcaatggcc tggcgcagta     900
ctctgtcctc ttttatggct attacgacaa taaacgcacg atcggatggc tgaatttccg     960
gctacctctt tcctacttcc tggtggggat tatgtgcatt ggatacagct tcctggttgt    1020
cctcaaagcg atgaccaaaa atattggtga cgatggtggt ggcgatgaca cactttcaa     1080 cttcagctgg aaggtgttct gtagctggga ctatctgatt ggtaaccctg aaacagccga    1140
caacaagttt aactctatca cgatgaactt taaggaagcc atcatagaag agagagccgc    1200
acaggtggag gagaacatcc acctcatcag atttctgagg tttctcgcta acttcttcgt    1260
gttcctcaca cttggtgcaa gtggataccc catcttttgg gctgtgaagc gatcccagga    1320
gttcgcccag caagatcctg acaccccttgg gtggtgggaa aaaaatgaaa tgaacatggt    1380
aatgtccctc ctggggatgt tctgtcccac cctgtttgac ttatttgctg aactggaaga    1440
ttaccatcct ctcattgctc tgaagtggct cctgggcgc attttttgctc ttcttctagg    1500 caacttgtat gtattcattc tcgccttgat ggatgagatt aacaacaaga ttgaagagga    1560
gaagcttgtg aaggctaata ttaccctgtg ggaagccaac atgattaagg cttacaatga    1620
atctctctct gggctctctg gaacaccac aggagcaccc ttttcgttc atcctgcaga    1680 tgtccctcgc ggtccctgct gggaaacaat ggtggggcag gaattcgtgc gtctcaccgt    1740
ttctgacgtc ctgaccactt acgtcacgat cctcattggc gacttcctca gagcatgttt    1800
cgtgaggttc tgcaattact gctggtgctg ggacttagaa tatggatatc cttcatacac    1860
agaattcgac atcagtggca acgtcctcgc tctgatcttc aaccaaggca tgatctggat    1920
gggctccttc ttcgctccta gcctcccggg catcaacatc ctccgtctcc acacatccat    1980
```

```
gtatttccag tgctgggctg tgatgtgctg caatgttccc gaggccaggg tgttcaaagc    2040
ttccagatcc aacaacttct acctcggcat gctgctactc atcctcttcc tgtccaccat    2100
gccagtcctg tacatgatcg tctccctccc gccatctttt gattgtgggc ccttcagtgg    2160
taaaaacagg atgtttgaag tcatcggtga gaccctggaa catgacttcc caagctggat    2220
ggcgaagatc ctgaggcagc tttctaaccc cggccttgtc attgctgtca ttctggtgat    2280
ggtcctgacc atctattatc tcaatgctac tgccaagggc cagaaagcag cgaatctgga    2340
cctcaaaaag aagatgaaac agcaagcttt ggagaacaaa atgcgaaaca gaaaatggc    2400 agcggctcga gcagctgcag ctgctggtgg ccagtaattt tatcaaatgt cctggaggtg    2460
cccagaagta ctcttcactt ctgtctttgt atggacagag tgagggccag tgaactgctg    2520
ctctatactc taccaccaat gcaccatcat ggcygcagtc atgaccatct gkcaaggaat    2580
catcagccct ctttgarcaa raaraatctc accattattt atgggaattt tttcaaagaa    2640
ttcttgaact cctcttcttc tctytctctc ctggacaaag kttctcaaac aaatgggagt    2700
ttaaatgtgg gtgtgatgta gtgatacaaa ttactgggta aaaatgatag gatactttaa    2760
aaaagtcaac atttcctcat atggactttt tcttacacac tggtctagtt tcttaaatga    2820
gaggagagct attacaacat cctttgctat ctaaatttgg aactatctgc atgaagcatt    2880
ccttgggatc attca                                                     2895

<210> SEQ ID NO 6
<211> LENGTH: 757
<212> TYPE: PRT
<213> ORGANISM: Mus musculus

<400> SEQUENCE: 6

Met Leu Gln Ile Gln Val Glu Glu Lys Glu Asp Thr Glu Glu Ser
1               5                   10                  15

Ser Ser Glu Glu Glu Asp Lys Leu Pro Arg Arg Glu Ser Leu Arg
                20                  25                  30

Pro Lys Arg Lys Arg Thr Arg Asp Val Ile Asn Glu Asp Pro Glu
            35                  40                  45

Pro Glu Pro Glu Asp Glu Glu Thr Arg Lys Ala Arg Glu Lys Glu Arg
        50                  55                  60

Arg Arg Arg Leu Arg Arg Gly Ala Glu Glu Glu Glu Ile Asp Glu
65                  70                  75                  80

Glu Glu Leu Glu Arg Leu Lys Ala Leu Leu Asp Glu Asn Arg Gln Met
                85                  90                  95

Ile Ala Thr Val Lys Cys Lys Pro Trp Lys Met Glu Lys Lys Ile Glu
            100                 105                 110

Val Leu Lys Glu Ala Lys Lys Phe Val Ser Glu Asn Glu Gly Ala Leu
        115                 120                 125

Gly Lys Gly Lys Gly Lys Lys Trp Phe Ala Phe Lys Met Met Met Ala
    130                 135                 140

Lys Lys Trp Ala Lys Phe Leu Arg Asp Phe Glu Asn Phe Lys Ala Ala
145                 150                 155                 160

Cys Val Pro Trp Glu Asn Lys Ile Lys Ala Ile Glu Ser Gln Phe Gly
                165                 170                 175

Ser Ser Val Ala Ser Tyr Phe Leu Phe Leu Arg Trp Met Tyr Gly Val
            180                 185                 190

Asn Met Val Leu Phe Val Leu Thr Phe Ser Leu Ile Met Leu Pro Glu
        195                 200                 205
```

```
Tyr Leu Trp Gly Leu Pro Tyr Gly Ser Leu Pro Arg Lys Thr Val Pro
    210                 215                 220

Arg Ala Glu Glu Ala Ser Ala Ala Asn Phe Gly Val Leu Tyr Asp Phe
225                 230                 235                 240

Asn Gly Leu Ala Gln Tyr Ser Val Leu Phe Tyr Gly Tyr Tyr Asp Asn
                245                 250                 255

Lys Arg Thr Ile Gly Trp Leu Asn Phe Arg Leu Pro Leu Ser Tyr Phe
            260                 265                 270

Leu Val Gly Ile Met Cys Ile Gly Tyr Ser Phe Leu Val Val Leu Lys
        275                 280                 285

Ala Met Thr Lys Asn Ile Gly Asp Asp Gly Gly Asp Asp Asn Thr
    290                 295                 300

Phe Asn Phe Ser Trp Lys Val Phe Cys Ser Trp Asp Tyr Leu Ile Gly
305                 310                 315                 320

Asn Pro Glu Thr Ala Asp Asn Lys Phe Asn Ser Ile Thr Met Asn Phe
                325                 330                 335

Lys Glu Ala Ile Ile Glu Glu Arg Ala Ala Gln Val Glu Glu Asn Ile
            340                 345                 350

His Leu Ile Arg Phe Leu Arg Phe Leu Ala Asn Phe Phe Val Phe Leu
        355                 360                 365

Thr Leu Gly Ala Ser Gly Tyr Leu Ile Phe Trp Ala Val Lys Arg Ser
    370                 375                 380

Gln Glu Phe Ala Gln Gln Asp Pro Asp Thr Leu Gly Trp Trp Glu Lys
385                 390                 395                 400

Asn Glu Met Asn Met Val Met Ser Leu Leu Gly Met Phe Cys Pro Thr
                405                 410                 415

Leu Phe Asp Leu Phe Ala Glu Leu Glu Asp Tyr His Pro Leu Ile Ala
            420                 425                 430

Leu Lys Trp Leu Leu Gly Arg Ile Phe Ala Leu Leu Leu Gly Asn Leu
        435                 440                 445

Tyr Val Phe Ile Leu Ala Leu Met Asp Glu Ile Asn Asn Lys Ile Glu
    450                 455                 460

Glu Glu Lys Leu Val Lys Ala Asn Ile Thr Leu Trp Glu Ala Asn Met
465                 470                 475                 480

Ile Lys Ala Tyr Asn Glu Ser Leu Ser Gly Leu Ser Gly Asn Thr Thr
                485                 490                 495

Gly Ala Pro Phe Phe Val His Pro Ala Asp Val Pro Arg Gly Pro Cys
            500                 505                 510

Trp Glu Thr Met Val Gly Gln Glu Phe Val Arg Leu Thr Val Ser Asp
        515                 520                 525

Val Leu Thr Thr Tyr Val Thr Ile Leu Ile Gly Asp Phe Leu Arg Ala
    530                 535                 540

Cys Phe Val Arg Phe Cys Asn Tyr Cys Trp Cys Trp Asp Leu Glu Tyr
545                 550                 555                 560

Gly Tyr Pro Ser Tyr Thr Glu Phe Asp Ile Ser Gly Asn Val Leu Ala
                565                 570                 575

Leu Ile Phe Asn Gln Gly Met Ile Trp Met Gly Ser Phe Phe Ala Pro
            580                 585                 590

Ser Leu Pro Gly Ile Asn Ile Leu Arg Leu His Thr Ser Met Tyr Phe
        595                 600                 605

Gln Cys Trp Ala Val Met Cys Cys Asn Val Pro Glu Ala Arg Val Phe
    610                 615                 620
```

```
Lys Ala Ser Arg Ser Asn Asn Phe Tyr Leu Gly Met Leu Leu Leu Ile
625                 630                 635                 640

Leu Phe Leu Ser Thr Met Pro Val Leu Tyr Met Ile Val Ser Leu Pro
            645                 650                 655

Pro Ser Phe Asp Cys Gly Pro Phe Ser Gly Lys Asn Arg Met Phe Glu
            660                 665                 670

Val Ile Gly Glu Thr Leu Glu His Asp Phe Pro Ser Trp Met Ala Lys
            675                 680                 685

Ile Leu Arg Gln Leu Ser Asn Pro Gly Leu Val Ile Ala Val Ile Leu
            690                 695                 700

Val Met Val Leu Thr Ile Tyr Tyr Leu Asn Ala Thr Ala Lys Gly Gln
705                 710                 715                 720

Lys Ala Ala Asn Leu Asp Leu Lys Lys Lys Met Lys Gln Gln Ala Leu
            725                 730                 735

Glu Asn Lys Met Arg Asn Lys Lys Met Ala Ala Arg Ala Ala Ala
            740                 745                 750

Ala Ala Gly Gly Gln
        755
```

<210> SEQ ID NO 7
<211> LENGTH: 3216
<212> TYPE: DNA
<213> ORGANISM: Mus musculus

<400> SEQUENCE: 7

```
tgcaagagtg gccaagtttg ccgggcgtgg tggcacacgc ctttaatccg agcactcggg      60
aggcagagga aggcgaattt ctgagttcaa ggccagcctg gtctacaaag tgagttccag     120
gacagccagg gctacacaga gaaaccctgt ctccaaaaac caaaaaaaaa aaaaaaaata     180
gtggccaagt tgttccaga ggcccctagt tgccgtcagg ttccaggaag aggccagtga      240
ccatgacagc aggaagtcac cccaggctgg cagtatatg aagacgtgag ccagtgtgag      300
ggccttgaaa ctctggtaac catgagcccc cagttaaaga gcttggacga ggaaggtgac     360
aagtcagcaa ggagacccac aaggaaacaa acctccagag ctgcatgtcc ccaagacggg     420
caccgagccc aatctagccg aaggatcct gctaagggta gcccaagacc agggtcttcc      480
cggaagaaac agatggaaca tggaagctat cacaaggggt tgcagggaca gaaaccacga     540
aaggtggaga ggtctctaca ggggaggaag aaggaccgga gaacttccct taaggagcag     600
agagcatctc caaagaagga gagggaggct ctgaggaagg aggcaggcaa gcagctgaga     660
aaacccaggt ccacttcctt gggctccagt gtctctactg gagactccct gtctgaggag     720
gagctggctc agatcctgga acaggtagaa gaaaaaaaga agctcatcac taccgtgagg     780
aacaaaccct ggcccatggc aaagaagctg agggaactca gggaagccca gcctttgtg     840
gagaagtatg aaggagcctt ggggaaaggc aagggcaaac acctctacgc ctacaggatg     900
atgatggcta agaaatgggt caagtttaag agggactttg ataatttcaa gactcaatgt     960
attccctggg aaatgaagat caaggacatt gaaagtcact tcggttcttc tgtggcatct    1020
tacttcatct tctccgatg gatgtatgga gttaaccttg tcctttttgg cttaatattt    1080
ggtctagtca tcatcccaga ggtgctgatg gcatgccct atggaagtat acccagaaag    1140
acggtgcctc gagctgagga gagcgagcc atggacttct ctgtcctttg ggattttgag    1200
ggctacatca atattctgc tctcttctat ggctactaca caaccagcg gaccattgga    1260
tggctgaggt acaggctgcc catggcttac tttatggtgg gggtcagcgt gtttggctac    1320
```

```
agcttgatga tcgtcattag gtcgatggcc agcaataccc agggtagcac cagtgagggg      1380
gacagtgaca gcttcacatt cagcttcaag atgttcacca gctgggacta cctcatcggg      1440
aattcagaga cagcagacaa caaatatgtc tccatcacta ccagcttcaa ggagtctata      1500
gtggacgaac aagagagtaa caaagaaggg aatatccacc tgacaagatt cctccgcgtc      1560
ctggccaact ttctcattct ctgctgtctg tgtggaagcg ggtacctcat ttactttgtg      1620
gtgaaacggt cccaggagtt ctccaaaatg caaaatgtca gctggtatga aggaatgag      1680
gtggagatcg tgatgtcttt gctagggatg ttttgtcccc ctctgtttga aaccatcgct      1740
gccttggaga attatcaccc acgaactggg ctgaagtggc agctgggccg catctttgcc      1800
ctcttcctgg gaaacctcta cacgtttctc ctggccctca tggacgatgt ccaccttaag      1860
cttctctaatg aggaaaaaat caagaacatc actcactgga ccctgtttaa ctattacaat      1920
tcctcaggtg ggaatgagag tgtgccccgg ccaccaccac accctgcaga tgtgcccaga      1980
ggttcttgct gggagacagc tgtgggcatt gagtttatga ggctcaccgt gtctgacatg      2040
ctggtaacat acctcaccat cttggtcgga gatttcctcc gagcttgttt tgtccggttc      2100
atgaatcact gctggtgttg ggacctcgag gctggttttc cctcatatgc cgagtttgat      2160
attagtggaa atgtgttggg tttgatcttc aaccaaggaa tgatctggat gggctccttc      2220
tatgctccag actggtggg catcaatgtc ctgcgcctgt tgacctccat gtacttccag      2280
tgctgggcag tgatgagcag caacgttccc cacgaacgtg tgtttaaagc ctccagatcc      2340
aacaacttct acatgggcct gctgctgttg gtgctcttcc tcagcctcct gcctgtggcc      2400
tacaccgtca tgtctctccc ccctcgtttt gactgtggcc ccttcagtgg aaaaacaga      2460
atgtacgatg tcctccatga gaccatcgag aacgatttcc ctaagttcct gggcaagatc      2520
tttgcgttcc ttgccaaccc aggcctgatc attccagcca tcctgctaat gtttctggcc      2580
atttactatc tgaactcagt ttcaaaaagt ctttctagag ctaatgccca gctgcgaaag      2640
aagatccaag cgctccgtga agttgagaag aaccataaat ccatcaaggg aaaagccata      2700
gtcacatatt cagaggacac aatcaagaac agctccaaaa atgccaccca gatacatctt      2760
actaaagaag agcccacatc tcactcttcc agccaaatcc agaccctgga caagaaagcg      2820
cagggccccc acacctccag tactgagggt ggggcctcgc catctacctc ctggcaccat      2880
gttgggtctc aaccaccgag aggcagacga gattctggcc aacccagtc tcagacttac      2940
acaggcaggt caccttctgg aaagagaacc cagaggcctc acaactgatt ttctggcatt      3000
catgggtgtc ccagtccttg gcttgaatct ctactgtttt atatatctct tcccttctca      3060
tctcacatat acaaatgttt ccctatggct tatgtaacat atgaacttta atccttgctt      3120
ccagcccttg attactacct aaagggaaga gcaatggacc tcacacacta gcggtttcct      3180
ttggctccag acttgaggag gcagggatga ggccat                                3216
```

<210> SEQ ID NO 8
<211> LENGTH: 888
<212> TYPE: PRT
<213> ORGANISM: Mus musculus

<400> SEQUENCE: 8

Met Ser Pro Gln Leu Lys Ser Leu Asp Glu Glu Gly Asp Lys Ser Ala
1               5                   10                  15

Arg Arg Pro Thr Arg Lys Gln Thr Ser Arg Ala Ala Cys Pro Gln Asp
            20                  25                  30

-continued

```
Gly His Arg Ala Gln Ser Ser Arg Lys Asp Pro Ala Lys Gly Ser Pro
         35                  40                  45

Arg Pro Gly Ser Ser Arg Lys Lys Gln Met Glu His Gly Ser Tyr His
 50                  55                  60

Lys Gly Leu Gln Gly Gln Lys Pro Arg Lys Val Glu Arg Ser Leu Gln
 65                  70                  75                  80

Gly Arg Lys Lys Asp Arg Arg Thr Ser Leu Lys Glu Gln Arg Ala Ser
                 85                  90                  95

Pro Lys Lys Glu Arg Glu Ala Leu Arg Lys Glu Ala Gly Lys Gln Leu
                100                 105                 110

Arg Lys Pro Arg Ser Thr Ser Leu Gly Ser Ser Val Ser Thr Gly Asp
            115                 120                 125

Ser Leu Ser Glu Glu Glu Leu Ala Gln Ile Leu Glu Gln Val Glu Glu
        130                 135                 140

Lys Lys Lys Leu Ile Thr Thr Val Arg Asn Lys Pro Trp Pro Met Ala
145                 150                 155                 160

Lys Lys Leu Arg Glu Leu Arg Glu Ala Gln Ala Phe Val Glu Lys Tyr
                165                 170                 175

Glu Gly Ala Leu Gly Lys Gly Lys Gly Lys His Leu Tyr Ala Tyr Arg
            180                 185                 190

Met Met Met Ala Lys Lys Trp Val Lys Phe Lys Arg Asp Phe Asp Asn
        195                 200                 205

Phe Lys Thr Gln Cys Ile Pro Trp Glu Met Lys Ile Lys Asp Ile Glu
    210                 215                 220

Ser His Phe Gly Ser Ser Val Ala Ser Tyr Phe Ile Phe Leu Arg Trp
225                 230                 235                 240

Met Tyr Gly Val Asn Leu Val Leu Phe Gly Leu Ile Phe Gly Leu Val
                245                 250                 255

Ile Ile Pro Glu Val Leu Met Gly Met Pro Tyr Gly Ser Ile Pro Arg
            260                 265                 270

Lys Thr Val Pro Arg Ala Glu Glu Arg Ala Met Asp Phe Ser Val
        275                 280                 285

Leu Trp Asp Phe Glu Gly Tyr Ile Lys Tyr Ser Ala Leu Phe Tyr Gly
    290                 295                 300

Tyr Tyr Asn Asn Gln Arg Thr Ile Gly Trp Leu Arg Tyr Arg Leu Pro
305                 310                 315                 320

Met Ala Tyr Phe Met Val Gly Val Ser Val Phe Gly Tyr Ser Leu Met
                325                 330                 335

Ile Val Ile Arg Ser Met Ala Ser Asn Thr Gln Gly Ser Thr Ser Glu
            340                 345                 350

Gly Asp Ser Asp Ser Phe Thr Phe Ser Phe Lys Met Phe Thr Ser Trp
        355                 360                 365

Asp Tyr Leu Ile Gly Asn Ser Glu Thr Ala Asp Asn Lys Tyr Val Ser
    370                 375                 380

Ile Thr Thr Ser Phe Lys Glu Ser Ile Val Asp Glu Gln Glu Ser Asn
385                 390                 395                 400

Lys Glu Gly Asn Ile His Leu Thr Arg Phe Leu Arg Val Leu Ala Asn
                405                 410                 415

Phe Leu Ile Leu Cys Cys Leu Cys Gly Ser Gly Tyr Leu Ile Tyr Phe
            420                 425                 430

Val Val Lys Arg Ser Gln Glu Phe Ser Lys Met Gln Asn Val Ser Trp
        435                 440                 445
```

-continued

```
Tyr Glu Arg Asn Glu Val Glu Ile Val Met Ser Leu Leu Gly Met Phe
450                 455                 460

Cys Pro Pro Leu Phe Glu Thr Ile Ala Ala Leu Glu Asn Tyr His Pro
465                 470                 475                 480

Arg Thr Gly Leu Lys Trp Gln Leu Gly Arg Ile Phe Ala Leu Phe Leu
                485                 490                 495

Gly Asn Leu Tyr Thr Phe Leu Leu Ala Leu Met Asp Asp Val His Leu
                500                 505                 510

Lys Leu Ser Asn Glu Glu Lys Ile Lys Asn Ile Thr His Trp Thr Leu
                515                 520                 525

Phe Asn Tyr Tyr Asn Ser Ser Gly Gly Asn Glu Ser Val Pro Arg Pro
530                 535                 540

Pro Pro His Pro Ala Asp Val Pro Arg Gly Ser Cys Trp Glu Thr Ala
545                 550                 555                 560

Val Gly Ile Glu Phe Met Arg Leu Thr Val Ser Asp Met Leu Val Thr
                565                 570                 575

Tyr Leu Thr Ile Leu Val Gly Asp Phe Leu Arg Ala Cys Phe Val Arg
                580                 585                 590

Phe Met Asn His Cys Trp Cys Trp Asp Leu Glu Ala Gly Phe Pro Ser
                595                 600                 605

Tyr Ala Glu Phe Asp Ile Ser Gly Asn Val Leu Gly Leu Ile Phe Asn
610                 615                 620

Gln Gly Met Ile Trp Met Gly Ser Phe Tyr Ala Pro Gly Leu Val Gly
625                 630                 635                 640

Ile Asn Val Leu Arg Leu Leu Thr Ser Met Tyr Phe Gln Cys Trp Ala
                645                 650                 655

Val Met Ser Ser Asn Val Pro His Glu Arg Val Phe Lys Ala Ser Arg
                660                 665                 670

Ser Asn Asn Phe Tyr Met Gly Leu Leu Leu Val Leu Phe Leu Ser
                675                 680                 685

Leu Leu Pro Val Ala Tyr Thr Val Met Ser Leu Pro Pro Ser Phe Asp
690                 695                 700

Cys Gly Pro Phe Ser Gly Lys Asn Arg Met Tyr Asp Val Leu His Glu
705                 710                 715                 720

Thr Ile Glu Asn Asp Phe Pro Lys Phe Leu Gly Lys Ile Phe Ala Phe
                725                 730                 735

Leu Ala Asn Pro Gly Leu Ile Ile Pro Ala Ile Leu Leu Met Phe Leu
                740                 745                 750

Ala Ile Tyr Tyr Leu Asn Ser Val Ser Lys Ser Leu Ser Arg Ala Asn
                755                 760                 765

Ala Gln Leu Arg Lys Lys Ile Gln Ala Leu Arg Glu Val Glu Lys Asn
                770                 775                 780

His Lys Ser Ile Lys Gly Lys Ala Ile Val Thr Tyr Ser Glu Asp Thr
785                 790                 795                 800

Ile Lys Asn Ser Ser Lys Asn Ala Thr Gln Ile His Leu Thr Lys Glu
                805                 810                 815

Glu Pro Thr Ser His Ser Ser Gln Ile Gln Thr Leu Asp Lys Lys
                820                 825                 830

Ala Gln Gly Pro His Thr Ser Thr Glu Gly Gly Ala Ser Pro Ser
                835                 840                 845

Thr Ser Trp His His Val Gly Ser Gln Pro Pro Arg Gly Arg Arg Asp
850                 855                 860
```

```
-continued

Ser Gly Gln Pro Gln Ser Gln Thr Tyr Thr Gly Arg Ser Pro Ser Gly
865                 870                 875                 880

Lys Arg Thr Gln Arg Pro His Asn
                885
```

NUCLEIC ACID ENCODING HUMAN TRANSDUCTIN-1 POLYPEPTIDE

CROSS-REFERENCE TO RELATED APPLICATIONS

This patent application is a divisional of U.S. patent application Ser. No. 10/487,887, filed Apr. 20, 2004, issued as U.S. Pat. No. 7,192,705, which is the U.S. National Phase of PCT/US02/29614, which was filed on Sep. 19, 2002 and which claims the benefit of U.S. Provisional Patent Application No. 60/323,275, which was filed on Sep. 19, 2001.

FIELD OF THE INVENTION

The present invention pertains to isolated or purified nucleic acids encoding transductin-1 (TDC1; now referred to as transmembrane cochlear-expressed gene 1 (TMC-1)), transductin-2 (TDC2; now referred to as transmembrane cochlear-expressed gene 2 (TMC2)), and fragments thereof, a vector comprising such a nucleic acid, a cell comprising such a vector, an isolated or purified polypeptide, a monoclonal antibody-producing cell line, a monoclonal antibody, pharmaceutically acceptable compositions of the above nucleic acids and polypeptides, and methods of diagnosis, prognosis and treatment of hearing loss, particularly DFNA 36 and DFNB 7/11-linked hearing loss.

BACKGROUND OF THE INVENTION

Hearing loss is a common communication disorder. Congenital hearing impairment occurs in approximately 1 in 1,000 children born in the United States. See Jain et al., A human recessive neurosensory nonsyndromic hearing impairment locus is a potential homologue of the murine deafness (dn) locus, *Human Molecular Genetics* 4(12): 2391-2394 (1995); and Scott et al., Refining the DFNB7-DFNB11 deafness locus using intragenic polymorphisms in a novel gene, TMEM2, *Gene* 246: 265-274 (2000). One to two percent of graduates of neonatal intensive care units also suffer such hearing impairment. See Jain et al. (1995), supra. Nearly 1 in 2 adults have functionally significant hearing loss by the eighth decade of life.

Deafness can be caused by a number of environmental and disease-related factors. In developed countries, however, at least 50% of the cases of deafness are inherited. See Scott et al. (2000), supra. Factors associated with an increased risk for hearing loss include male gender, exposure to aminoglycoside antibiotics, exposure to noise, head trauma, and barotraumas. The majority of cases seem to involve single gene mutations, as there is no additional clinical anomaly, and an autosomal recessive mode of inheritance predominates. Nonsyndromic hereditary hearing impairment (NSHHI) is considered to be highly heterogeneous, and is thought to be caused by a large number of genes.

Vertebrates detect sounds, body accelerations and water movements with the acoustico-lateralis sensory system (Hudspeth et al., Sensitivity, polarity, and conductance change in the response of vertebrate hair cells to controlled mechanical stimuli, *Proc. Natl. Acad. Sci. USA* 74(6): 2407-2411 (1977)). The primary receptors of this system are neuroepithelial cells termed hair cells. Each of these cells has a "hair bundle" on its apical surface, which is comprised of an elongated microvillus (stereocilium) and, in most cases, a single true cilium (kinocilium). Vibrations, such as from sound waves, stimulate the cells by bending the hair bundles. Bending of the hair bundles leads to the production of a small receptor potential, which excites afferent nerve fibers by chemical or electrical synapses. The exact mechanism of the production of the potential is not yet known, with the existence of conflicting data as to the ions involved in creating the potential (Corey et al., Ionic basis of the receptor potential in a vertebrate hair cell, *Nature* 281: 675-77 (1979)).

Thus far, linkage studies have been the primary method employed to identify potential loci implicated in hereditary deafness. However, single families suitable in size for conventional linkage analysis are not common. NSHHI also lends itself poorly to subclassification by audiometric criteria. Thus, traditional studies have used consanguineous families from geographically isolated populations to map several different loci which are associated with recessive NSHHI (Jain et al. (1995), supra). In humans certain forms of NSHHI have been found to localize to a region of chromosome 9. See, e.g. Kurima et al., Genetic map localization of DFNA34 and DFNA36, two novel autosomal dominant nonsyndromic deafness loci, *ARO Abstracts* 24:265 (2001); and Scott et al. (2000), supra. Scott et al. identified a gene in the relevant region of the chromosome; however, it was poorly correlated to hearing loss at the particular locus, as the protein was expressed in a variety of other tissues, such as the heart, brain, spleen, lung, liver, muscle and kidney, and no difference in transcript size or expression level was apparent between normal and deaf mice by Northern blot analysis.

In view of the above, it is an object of the present invention to provide a gene that correlates well with hearing loss as well as the encoded polypeptide and related vectors, host cells, polypeptides, antibodies, antibody-producing cell lines and methods of diagnosing, prognosticating and treating hearing loss. These and other objects and advantages of the present invention, as well as additional inventive features, will be apparent from the description of the invention provided herein.

BRIEF SUMMARY OF THE INVENTION

The present invention provides an isolated or purified nucleic acid molecule consisting essentially of a nucleotide sequence encoding TDC1 or a fragment thereof comprising at least 314 contiguous nucleotides, and an isolated or purified nucleic acid molecule consisting essentially of a nucleotide sequence that is complementary to a nucleotide sequence encoding human TDC1 or a fragment thereof.

The present invention further provides an isolated or purified nucleic acid molecule consisting essentially of a nucleotide sequence encoding TDC2 or a fragment thereof comprising at least 110 contiguous nucleotides, and an isolated or purified nucleic acid molecule consisting essentially of a nucleotide sequence that is complementary to a nucleotide sequence encoding human TDC2 or a fragment thereof.

Also provided by the present invention is a vector comprising one of the above-described isolated or purified nucleic acid molecules. Further provided is a cell comprising one of the above-identified nucleic acid molecules. Also provided is a composition comprising one of the above identified isolated or purified nucleic acid molecules or vectors and a pharmaceutically acceptable carrier.

An isolated or purified polypeptide molecule consisting essentially of an amino acid sequence encoding TDC1 or a fragment thereof comprising at least 95 contiguous amino acids, which is optionally glycoslyated, amidated, carboxylated, phosphorylated, esterified, N-acylated or converted into an acid addition salt, is also provided.

An isolated or purified polypeptide molecule consisting essentially of an amino acid sequence encoding TDC2 or a fragment thereof comprising at least 71 contiguous amino acids, which is optionally glycoslyated, amidated, carboxylated, phosphorylated, esterified, N-acylated or converted into an acid addition salt, is further provided.

Also provided is a composition comprising an above-described isolated or purified polypeptide molecule and a pharmaceutically acceptable carrier. Further provided is a cell line that produces a monoclonal antibody that is specific for an above-described isolated or purified polypeptide molecule. Still further provided is the antibody produced by the above-mentioned cell-line.

Methods of detecting hearing loss or a predisposition to hearing loss in an animal are also provided. In one embodiment, the method comprises detecting at least one mutation in a gene encoding TDC1 in a test sample comprising a nucleic acid comprising the TDC1 gene obtained from the animal, wherein the at least one mutation is indicative of hearing loss or a predisposition to hearing loss in the animal. The hair cell can be of the inner ear of the animal. In another embodiment, the method comprises detecting at least one mutation in a gene encoding TDC2 in a test sample comprising a nucleic acid comprising the TDC2 gene obtained from the animal, wherein the at least one mutation is indicative of hearing loss or a predisposition to hearing loss in the animal.

Also provided is a method of determining the level of nucleic acid comprising the wild-type TDC1 gene and/or a mutant TDC1 gene in a test sample comprising a nucleic acid comprising the wild-type TDC1 gene and/or a mutant TDC1 gene obtained from an animal. The method comprises assaying the test sample for the level of nucleic acid comprising the wild-type TDC1 gene and/or a mutant TDC1 gene, wherein a decrease in the level of nucleic acid comprising the wild-type TDC1 gene and/or an increase in the level of nucleic acid comprising a mutant TDC1 gene in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

Further provided is a method of determining the level of nucleic acid comprising the wild-type TDC2 gene and/or a mutant TDC2 gene in a test sample comprising a nucleic acid comprising the wild-type TDC2 gene and/or a mutant TDC2 gene obtained from an animal. The method comprises assaying the test sample for the level of nucleic acid comprising the wild-type TDC2 gene and/or a mutant TDC2 gene, wherein a decrease in the level of nucleic acid comprising the wild-type TDC2 gene and/or an increase in the level of nucleic acid comprising a mutant TDC2 gene in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

Methods for detecting hearing loss or a predisposition to hearing loss in an animal are also provided. In one embodiment, the method comprises detecting a mutant TDC1 in a test sample comprising protein comprising TDC1 obtained from the animal, wherein the presence of a mutant TDC1 in the test sample is indicative of hearing loss or a predisposition to hearing loss in the animal. In another embodiment, the method comprises detecting a mutant TDC2 in a test sample comprising protein comprising TDC2 obtained from the animal, wherein the presence of a mutant TDC2 in the test sample is indicative of hearing loss or a predisposition to bearing loss in the animal.

Also provided is a method of determining the level of wild-type TDC1 and/or a mutant TDC1 in a test sample comprising protein comprising wild-type TDC1 and/or a mutant TDC1 obtained from an animal. The method comprises assaying the test sample for the level of wild-type TDC1 and/or a mutant TDC1, wherein a decrease in the level of wild-type TDC1 and/or an increase in the level of a mutant TDC1 in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

Also provided is a method of determining the level of wild-type TDC2 and/or a mutant TDC2 in a test sample comprising protein comprising wild-type TDC2 and/or a mutant TDC2 obtained from an animal. The method comprises assaying the test sample for the level of wild-type TDC2 and/or a mutant TDC2, wherein a decrease in the level of wild-type TDC2 and/or an increase in the level of a mutant TDC2 in the test sample as compared to a control sample is indicative of hearing loss or a predisposition to hearing loss in the animal. The method can be used to prognosticate hearing loss or to assess the efficacy of treatment of hearing loss with a given anti-hearing loss agent in accordance with methods set forth herein.

The invention further provides a method of treating an animal prophylactically or therapeutically for hearing loss, wherein the hearing loss is due to a complete or partial loss of wild-type TDC1, which method comprises providing TDC1 to the animal, whereupon the animal is treated prophylactically or therapeutically for hearing loss. The TDC1 can be provided to the animal by administering to the animal a nucleic acid encoding and expressing wild-type TDC1. The TDC1 also can be provided to the animal by administering to the animal the wild-type TDC1 protein.

The invention still further provides a method of treating an animal prophylactically or therapeutically for hearing loss, wherein the hearing loss is due to a complete or partial loss of wild-type TDC2, which method comprises providing TDC2 to the animal, whereupon the animal is treated prophylactically or therapeutically for hearing loss. The TDC2 can be provided to the animal by administering to the animal a nucleic acid encoding and expressing wild-type TDC2. The TDC2 also can be provided to the animal by administering to the animal the wild-type TDC2 protein.

Further provided is a method of identifying one or more agents which interact with a TDC1 gene and/or a TDC2 gene in a cell, comprising administering one or more agents to the cell comprising the TDC1 gene and/or the TDC2 gene and assaying the expression level of the TDC1 gene and/or the TDC2 gene by the cell, wherein an increase or decrease in the expression level of the TDC1 gene and/or the TDC2 gene is indicative of an interaction between one or more agents and the TDC1 gene and/or the TDC2 gene in the cell.

BRIEF DESCRIPTION OF THE FIGURES

FIG. 1 represents the nucleotide (SEQ ID NO: 1) and deduced amino acid (SEQ ID NO: 2) full-length sequences of human TDC1 cDNA.

FIG. 2 represents the nucleotide (SEQ ID NO: 3) and deduced amino acid (SEQ ID NO: 4) full-length sequences of human TDC2 cDNA.

FIG. 3 represents the nucleotide (SEQ ID NO: 5) and deduced amino acid (SEQ ID NO: 6) full-length sequences of mouse TDC1 cDNA.

FIG. 4 represents the nucleotide (SEQ ID NO: 7) and deduced amino acid (SEQ ID NO: 8) full-length sequences of mouse TDC2 cDNA.

DETAILED DESCRIPTION OF THE INVENTION

The TDC1 and TDC2 genes are implicated in DFNA 36- and DFNB 7/11-linked hearing loss, two forms of hereditary deafness. These genes also may be, at least in part, the cause of certain forms of non-hereditary deafness, or other forms of hereditary deafness. These genes encode a mechanotransduction channel of an animal hair cell, particularly hair cells of the inner ear. These cells are responsible for turning mechanical stimulation (such as sound waves) into chemical signals which can be processed by the brain. Any abnormality in the normal expression of this mechanotransduction channel can lead to hearing loss. This abnormal expression may result from mutations or deletions in the sequence or in the sequences surrounding the particular gene, or from other genetic abnormalities as are known in the art. Particularly, the mutation(s) can compromise the ability of the TDC1 and/or TDC2 gene product to form a component of a hair cell of the inner ear of the animal, thereby causing hearing loss. The mutation(s) can also compromise the ability of the TDC1 and/or TDC2 gene product to form all or some of an ion transduction channel of the hair cell of the inner ear of the animal. Further, the mutation(s) can compromise the mechanosensory activity of the TDC1 and/or TDC2 gene product. Hearing loss can mean either the entire loss or partial loss of hearing as would be understood by an ordinarily skilled artisan. The hearing loss can be hereditary, sensorineural hearing loss, nonsyndromic autosomal-dominant hearing loss, and/or DFNA 36- or DFNB 7/11-linked hearing loss.

Mutations in TDC1 and/or TDC2 can cause deafness. In particular, dominant mutations can cause childhood-onset, rapidly progressive, bilateral sensorineural hearing loss. Several recessive mutations can cause congenital, profound bilateral sensorineural deafness. Several of the recessive mutations can also result in functional null alleles: nonsense mutations, genomic deletion of two exons, or frameshift mutations.

Any animal with hair cells within their auditory receptor can benefit from the present invention. Desirably, the animal is a mammal, preferably a human. However, animals such as birds, especially chickens, also can benefit from the present invention.

The present invention provides an isolated or purified nucleic acid molecule consisting essentially of a nucleotide sequence encoding transductin or a fragment thereof. By transductin is meant TDC1 and/or TDC2, preferably of an animal, and even more preferably of a human. By "isolated" is meant the removal of transductin from its natural environment. By "purified" is meant that transductin, whether it has been removed from nature or synthesized and/or amplified under laboratory conditions, has been increased in purity, wherein "purity" is a relative term, not "absolute purity." "Nucleic acid molecule" is intended to encompass a polymer of DNA or RNA, i.e., a polynucleotide, which can be single-stranded or double-stranded and which can contain non-natural or altered nucleotides. Moreover, the nucleic acids and genes can comprise exons, introns, and/or regulatory regions and elements.

Preferably, the isolated or purified nucleic acid molecule consists essentially of a nucleotide sequence encoding TDC1 or a fragment thereof comprising at least 314 contiguous nucleotides. The TDC1 can be a human TDC1. In a preferred embodiment, the isolated or purified nucleic acid molecule can encode the amino acid sequence of SEQ ID NO: 2 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, the isolated or purified nucleic acid molecule consists essentially of the nucleotide sequence of SEQ ID NO: 1 or a fragment thereof comprising at least 314 contiguous nucleotides. More preferably, the fragment comprises at least 320 contiguous nucleotides. Still more preferably, the fragment comprises at least 330 contiguous nucleotides. Even more preferably, the fragment comprises at least 340 contiguous nucleotides. Further, the isolated or purified nucleic acid molecule can hybridize under moderately stringent conditions to an isolated or purified nucleic acid molecule consisting essentially of the nucleotide sequence that is complementary to SEQ ID NO: 1 or a fragment thereof, such as naturally occurring and artificially generated variants. Alternatively, but still preferably, the isolated or purified nucleic acid molecule can share 43% or more identity with SEQ ID NO: 1, such as naturally occurring and artificially generated variants. Also preferably, the isolated or purified nucleic acid molecule can share 50% or more identity with SEQ ID NO: 1. More preferably, the isolated or purified nucleic acid molecule can share 70% or more identity with SEQ ID NO: 1. Still more preferably, the isolated or purified nucleic acid molecule can share 90% or more identity with SEQ ID NO: 1.

Alternatively, the isolated or purified nucleic acid molecule can encode the amino acid sequence of SEQ ID NO: 6 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, the isolated or purified nucleic acid molecule consists essentially of the nucleotide sequence of SEQ ID NO: 5 or a fragment thereof comprising at least 314 contiguous nucleotides.

More preferably, the fragment comprises at least 320 contiguous nucleotides. Still more preferably, the fragment comprises at least 330 contiguous nucleotides. Even more preferably, the fragment comprises at least 340 contiguous nucleotides. Further, the isolated or purified nucleic acid molecule can hybridize under moderately stringent conditions to an isolated or purified nucleic acid molecule consisting essentially of the nucleotide sequence that is complementary to SEQ ID NO: 5 or a fragment thereof such as naturally occurring and artificially generated variants. Alternatively, but still preferably, the isolated or purified nucleic acid molecule can share 40% or more identity with SEQ ID NO: 5, such as naturally occurring and artificially generated variants. Also preferably, the isolated or purified nucleic acid molecule can share 45% or more identity with SEQ ID NO: 5. More preferably, the isolated or purified nucleic acid molecule can share 60% or more identity with SEQ ID NO: 5. Still more preferably, the isolated or purified nucleic acid molecule can share 80% or more identity with SEQ ID NO: 5.

Also preferably, the isolated or purified nucleic acid molecule consists essentially of a nucleotide sequence encoding TDC2 or a fragment thereof comprising at least 110 contiguous nucleotides. The TDC2 can be a human TDC2. In a preferred embodiment, the isolated or purified nucleic acid molecule can encode the amino acid sequence of SEQ ID NO: 4 or a fragment thereof comprising at least 70 contiguous amino acids. More preferably, the fragment comprises at least 75 contiguous amino acids. Still more preferably, the fragment comprises at least 80 contiguous amino acids. Even more preferably, the fragment comprises at least 85 contiguous amino acids. Alternatively, the isolated or purified nucleic acid molecule consists essentially of the nucleotide sequence of SEQ ID NO: 3 or a fragment thereof comprising at least 110 contiguous nucleotides. More preferably, the fragment comprises at least 115 contiguous nucleotides. Still more preferably, the fragment comprises at least 130 contiguous nucleotides. Even more preferably, the fragment comprises at least 150 contiguous nucleotides. In a further preferred embodiment, the isolated or purified nucleic acid molecule can hybridize under moderately stringent conditions to an isolated or purified nucleic acid molecule consisting essentially of the nucleotide sequence that is complementary to SEQ ID NO: 3 or a fragment thereof. Alternatively, but still preferably, the isolated or purified nucleic acid molecule can share 49% or more identity with SEQ ID NO: 3. Also preferably, the isolated or purified nucleic acid molecule can share 55% or more identity with SEQ ID NO: 3. More preferably, the isolated or purified nucleic acid molecule can share 70% or more identity with SEQ ID NO: 3. Still more preferably, the isolated or purified nucleic acid molecule can share 90% or more identity with SEQ ID NO: 3.

Alternatively, but still preferably, the isolated or purified nucleic acid molecule can encode the amino acid sequence of SEQ ID NO:8 or a fragment thereof comprising at least 71 contiguous amino acids. Also preferably, the isolated or purified nucleic acid molecule can consist essentially of the nucleotide sequence of SEQ ID NO: 7 or a fragment thereof comprising at least 110 contiguous nucleotides. More preferably, the fragment comprises at least 115 contiguous nucleotides. Still more preferably, the fragment comprises at least 120 contiguous nucleotides, Even more preferably, the fragment comprises at least 125 nucleotides. In a farther preferred embodiment, the fragment can hybridize under moderately stringent conditions to an isolated or purified nucleic acid molecule consisting essentially of the nucleotide sequence that is complementary to SEQ ID NO: 7 or a fragment thereof. In an alternative embodiment, the isolated or purified nucleic acid molecule can share 41% or more identity with SEQ ID NO: 7. Alternatively, but still preferably, the isolated or purified nucleic acid molecule can share 55% or more identity with SEQ ID NO: 7. More preferably, the isolated or purified nucleic acid molecule can share 75% or more identity with SEQ ID NO: 7. Still more preferably, the isolated or purified nucleic acid molecule can share 90% or more identity with SEQ ID NO: 7.

An isolated or purified nucleic acid molecule consisting essentially of a nucleotide sequence encoding a variant TDC1 or a fragment thereof can comprise one or more insertions, deletions, inversions and/or substitutions. Desirably, the variant TDC1 does not differ functionally from the corresponding unmodified TDC1 or a fragment thereof comprising at least 314 contiguous nucleotides, such as that comprising SEQ ID NO: 1. Preferably, the one or more substitution(s) results in the substitution of an amino acid of the encoded TDC1 with another amino acid of approximately equivalent mass, structure and charge.

An isolated or purified nucleic acid molecule consisting essentially of a nucleotide sequence encoding a variant TDC2 or a fragment thereof can comprise one or more insertions, deletions, inversions and/or substitutions. Desirably, the variant TDC2 does not differ functionally from the corresponding unmodified TDC2 or a fragment thereof comprising at least 110 contiguous nucleotides, such as that comprising SEQ ID NO: 3. Preferably, the one or more substitution(s) results in the substitution of an amino acid of the encoded TDC2 with another amino acid of approximately equivalent mass, structure and charge.

The present invention also provides an isolated or purified nucleic acid molecule consisting essentially of a nucleotide sequence that is complementary to a nucleotide sequence encoding human TDC1 or a fragment thereof. Such an isolated or purified nucleic acid molecule preferably is complementary to a nucleotide sequence encoding the amino acid sequence of SEQ ID NO: 2 or a fragment thereof comprising at least 105 contiguous amino acids. More preferably, the fragment comprises at least 110 contiguous amino acids. Still more preferably, the fragment comprises at least 115 contiguous amino acids. Even more preferably, the fragment comprises at least 120 contiguous amino acids. Alternatively, but still preferably, the isolated or purified nucleic acid molecule is complementary to the nucleotide sequence of SEQ ID NO: 1 or a fragment thereof comprising at least 314 contiguous nucleotides. In another preferred embodiment, the isolated or purified nucleic acid molecule hybridizes under moderately stringent conditions to an isolated or purified nucleic acid molecule consisting essentially of SEQ ID NO: 1 or a fragment thereof Preferably, the isolated or purified nucleic acid molecule shares 43% or more identity with the nucleotide sequence that is complementary to SEQ ID NO: 1. More preferably, the isolated or purified nucleic acid molecule shares 50% or more identity with SEQ ID NO: 1. Even more preferably, the isolated or purified nucleic acid molecule shares 70% or more sequence identity with SEQ ID NO: 1. Still more preferably, the isolated or purified nucleic acid molecule shares 90% or more sequence identity with SEQ ID NO: 1. An isolated or purified nucleic acid molecule consisting essentially of a nucleotide sequence that is complementary to either of a nucleotide sequence encoding a variant TDC1 or a fragment thereof also can be obtained.

The present invention also provides an isolated or purified nucleic acid molecule consisting essentially of a nucleotide sequence that is complementary to either of a nucleotide sequence encoding human TDC2 or a fragment thereof. Such an isolated or purified nucleic acid molecule preferably is complementary to a nucleotide sequence encoding the amino acid sequence of SEQ ID NO: 4 or a fragment thereof comprising at least 70 contiguous amino acids. More preferably, the fragment comprises at least 75 contiguous amino acids. Still more preferably, the fragment comprises at least 80 contiguous amino acids. Even more preferably, the fragment comprises at least 85 contiguous amino acids. Alternatively, but still preferably, the isolated or purified nucleic acid molecule is complementary to the nucleotide sequence of SEQ ID NO: 3 or a fragment thereof comprising at least 110 contiguous nucleotides. In another preferred embodiment, the isolated or purified nucleic acid molecule hybridizes under moderately stringent conditions to an isolated or purified nucleic acid molecule consisting essentially of SEQ ID NO: 3 or a fragment thereof. Preferably, the isolated or purified nucleic acid molecule shares 49% or more identity with the nucleotide sequence that is complementary to SEQ ID NO: 3. More preferably, the isolated or purified nucleic acid molecule shares 55% or more identity with SEQ ID NO: 3. Even more preferably, the isolated or purified nucleic acid molecule shares 75% or more sequence identity with SEQ ID NO: 3. Still more preferably, the isolated or purified nucleic acid molecule shares 90% or more sequence identity with SEQ ID NO: 3. An isolated or purified nucleic acid molecule consisting essentially of a nucleotide sequence that is complementary to either of a nucleotide sequence encoding a variant TDC2 or a fragment thereof also can be obtained.

Whereas embodiments of the present invention are described in the context of applications to humans, the teachings set forth herein can be adapted to other animals as a matter of routine experimentation. For example, further disclosed herein are the sequences for a mouse TDC1 (SEQ ID NOS: 5 (nucleic acid) and 6 (amino acid)) and a mouse TDC2 (SEQ ID NOS: 7 (nucleic acid) and 8 (amino acid)). These sequences also can be used in the context of the present invention and constitute alternative preferred embodiments.

With respect to the above, one of ordinary skill in the art knows how to generate insertions, deletions, inversions and/or substitutions in a given nucleic acid molecule. See, for example, the references cited herein under "Example." It is preferred that the one or more substitution(s) result(s) in the substitution of an amino acid with another amino acid of approximately equivalent mass, structure and charge.

Also with respect to the above, "does not differ functionally from" is intended to mean that the variant transductin has activity characteristic of the unmodified transductin. In other words, it regulates a transductin-responsive gene. However, the variant transductin can be more or less active than the unmodified transductin as desired in accordance with the present invention.

An indication that polynucleotide sequences are substantially identical is if two molecules selectively hybridize to each other under moderately stringent conditions. The phrase "hybridizes to" refers to the selective binding of a single-stranded nucleic acid probe to a single-stranded target DNA or RNA sequence of complementary sequence when the target sequence is present in a preparation of heterogeneous DNA and/or RNA. "Moderately stringent conditions" are sequence-dependent and will be different in different circumstances. Generally, moderately stringent conditions are selected to be about 20° C. lower than the thermal melting point (Tm) for the specific sequence at a defined ionic strength and pH. The Tm is the temperature (under defined ionic strength and pH) at which 50% of the target sequence hybridizes to a perfectly matched probe.

For example, under moderately stringent conditions, as that term is understood by one skilled in the art, hybridization is preferably carried out using a standard hybridization buffer at a temperature ranging from about 50° C. to about 75° C., even more preferably from about 60° C. to about 70° C., and optimally from about 65° C. to about 68° C. Alternately, formamide can be included in the hybridization reaction, and the temperature of hybridization can be reduced to preferably from about 35° C. to about 45° C., even more preferably from about 40° C. to about 45° C., and optimally to about 42° C. Desirably, formamide is included in the hybridization reaction at a concentration of from about 30% to about 50%, preferably from about 35% to about 45%, and optimally at about 40%. Moreover, optionally, the hybridized sequences are washed (if necessary to reduce non-specific binding) under relatively highly moderately stringent conditions, as that term is understood by those skilled in the art. For instance, desirably, the hybridized sequences are washed one or more times using a solution comprising salt and detergent, preferably at a temperature of from about 50° C. to about 75° C., even more preferably at from about 60° C. to about 70° C., and optimally from about 65° C. to about 68° C. Preferably, a salt (e.g., such as sodium chloride) is included in the wash solution at a concentration of from about 0.01 M to about 1.0 M. Optimally, a detergent (e.g., such as sodium dodecyl sulfate) is also included at a concentration of from about 0.01% to about 1.0%.

The following are examples of highly stringent and moderately stringent conditions for a Southern hybridization in aqueous buffers (no formamide) (Sambrook and Russell, *Molecular Cloning*, 3rd Ed. SCHL Press (2001)):

| Highly stringent hybridization conditions: | Moderately Stringent hybridization conditions: |
|---|---|
| 6X SSC or 6X SSPE 5x Denhardt's Reagent 1% SDS 100 µg/ml salmon sperm DNA hybridization at 65-68° C. | 6X SSC or 6X SSPE 5x Denhardt's Reagent 1% SDS 10 µg/ml salmon sperm DNA hybridization at 58-64° C. |
| Highly stringent washing conditions: | Moderately stringent washing conditions: |
| 0.1X SSC/0.1% SDS washing at 65-68° C. | 2X SSC/0.1% SDS washing at 58-64° C. |

In view of the above, "stringent conditions" preferably allow for about 20% mismatch, more preferably up to about 15% mismatch, and most preferably up to about 5% mismatch, such as 4%, 3%, 2%, or 1% mismatch. "At least moderately stringent conditions" preferably allow for up to about 40% mismatch, more preferably up to about 30% mismatch, and most preferably up to about 20% mismatch. "Low stringency conditions" preferably allow for up to about 60% mismatch, more preferably up to about 50% mismatch, and most preferably up to about 40% mismatch. With respect to the preceding ranges of mismatch, 1% mismatch corresponds to one degree decrease in the melting temperature.

The above isolated or purified nucleic acid molecules also can be characterized in terms of "percentage of sequence identity." In this regard, a given nucleic acid molecule as described above can be compared to a nucleic acid molecule encoding a corresponding gene (i.e., the reference sequence) by optimally aligning the nucleic acid sequences over a comparison window, wherein the portion of the polynucleotide sequence in the comparison window may comprise additions or deletions (i.e., gaps) as compared to the reference sequence, which does not comprise additions or deletions, for optimal alignment of the two sequences. The percentage of sequence identity is calculated by determining the number of positions at which the identical nucleic acid base occurs in both sequences, i.e., the number of matched positions, dividing the number of matched positions by the total number of positions in the window of comparison, and multiplying the result by 100 to yield the percentage of sequence identity. Optimal alignment of sequences for comparison may be conducted by computerized implementations of known algorithms (e.g., GAP, BESTFIT, FASTA, and TFASTA in the Wisconsin Genetics Software Package, Genetics Computer Group (GCG), 575 Science Dr., Madison, Wis., or BlastN and BlastX available from the National Center for Biotechnology Information, Bethesda, Md.), or by inspection. Sequences are typically compared using BESTFIT or BlastN with default parameters.

"Substantial sequence identity" means that at least 75%, preferably at least 80%, more preferably at least 90%, and most preferably at least 95% (such as 96%, 97%, 98% or 99%) of the sequence of a given nucleic acid molecule is identical to a given reference sequence. Typically, two polypeptides are considered to be substantially similar if at least 40%, preferably at least 60%, more preferably at least 90%, and most preferably at least 95% (such as 96%, 97%, 98% or 99%) of the amino acids of which the polypeptides are comprised are identical to or represent conservative substitutions of the amino acids of a given reference sequence.

One of ordinary skill in the art will appreciate, however, that two polynucleotide sequences can be substantially different at the nucleic acid level, yet encode substantially similar, if not identical, amino acid sequences, due to the degeneracy of the genetic code. The present invention is intended to encompass such polynucleotide sequences.

While the above-described nucleic acid molecules can be isolated or purified, alternatively they can be synthesized. Methods of nucleic acid synthesis are known in the art. See, e.g., the references cited herein under "Examples."

The above-described nucleic acid molecules can be used, in whole or in part (i.e., as fragments or primers), to identify and isolate corresponding genes from other organisms for use in the context of the present inventive method using conventional means known in the art. See, for example, the references cited herein under "Examples."

In view of the above, the present invention also provides a vector comprising an above-described isolated or purified nucleic acid molecule. A nucleic acid molecule as described above can be cloned into any suitable vector and can be used to transform or transfect any suitable host. The selection of vectors and methods to construct them are commonly known to persons of ordinary skill in the art and are described in general technical references (see, in general, "Recombinant DNA Part D," *Methods in Enzymology*, Vol. 153, Wu and Grossman, eds., Academic Press (1987) and the references cited herein under "Examples"). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

Constructs of vectors, which are circular or linear, can be prepared to contain an entire nucleic acid sequence as described above or a portion thereof ligated to a replication system functional in a prokaryotic or eukaryotic host cell. Replication systems can be derived from ColE1, 2 mµ plasmid, λ, SV40, bovine papillomavirus, and the like.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. A preferred cloning vector is selected from the group consisting of the pUC series the pBluescript series (Stratagene, LaJolla, Calif.), the pET series (Novagen, Madison, Wis.), the pGEX series (Pharmacia Biotech, Uppsala, Sweden), and the pEX series (Clonetech, Palo Alto, Calif.). Bacteriophage vectors, such as λGT10, λGT11, λZapII (Stratagene), λ EMBL4, and λ NM1149, also can be used. Examples of plant expression vectors include pBI101, pBI101.2, pBI101.3, pBI121 and pBIN19 (Clonetech, Palo Alto, Calif.). Examples of animal expression vectors include pEUK-C1, pMAM and pMAM-neo (Clonetech).

An expression vector can comprise a native or nonnative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule as described above with a promoter is also within the skill in the art.

Also in view of the above, the present invention provides a cell comprising an isolated or purified nucleic acid molecule or a vector as described above. Examples of suitable cells include, but are not limited to, a human cell, a human cell line, *E. coli*, (e.g., *E. coli* TB-1, TG-2, DH5α, XL-Blue MPF' (Stratagene), SA2821 and Y1090) *B. subtlius, P. aerugenosa, S. cerevtsiae*, and *N. crassa*.

The present invention further provides an isolated or purified polypeptide molecule consisting essentially of an amino acid sequence encoding TDC1 or a fragment thereof comprising at least 95 contiguous amino acids, either one of which is optionally glycosylated, amidated, carboxylated, phosphorylated, esterified, N-acylated or converted into an acid addition salt. The isolated or purified polypeptide molecule is preferably obtained from a mammalian source. Even more preferably, the mammalian source is a human. The isolated or purified polypeptide molecule can be encoded by the nucleotide sequence of SEQ ID NO: 1 or a fragment thereof comprising at least 285 contiguous nucleotides. Preferably, the isolated or purified polypeptide molecule consists essentially of the amino acid sequence of SEQ ID NO: 2 or a fragment thereof comprising at least 95 contiguous amino acids. More preferably, the fragment comprises at least 100 contiguous amino acids. Still more preferably, the fragment comprises at least 105 contiguous amino acids. Even more preferably, the fragment comprises at least 110 contiguous amino acids. Alternatively, but still preferably, the isolated or purified polypeptide molecule shares 24% or more identity with SEQ ID NO: 2. More preferably, the isolated or purified polypeptide molecule shares 30% or more identity with SEQ ID NO: 2. Still more preferably, the isolated or purified polypeptide molecule shares 45% or more identity with SEQ ID NO: 2. Even more preferably, the isolated or purified polypeptide molecule shares 65% or more identity with SEQ ID NO: 2.

In a further embodiment, the isolated or purified polypeptide molecule can be encoded by the nucleotide sequence of SEQ ID NO: 5 or a fragment thereof comprising at least 285 contiguous nucleotides. Additionally, the isolated or purified polypeptide molecule can consist essentially of the amino acid sequence of SEQ ID NO: 6 or a fragment thereof comprising at least 95 contiguous amino acids. More preferably, the fragment comprises at least 100 contiguous amino acids. Still more preferably, the fragment comprises at least 115 contiguous amino acids. Even more preferably, the fragment comprises at least 130 contiguous amino acids. Alternatively, the isolated or purified polypeptide molecule shares 25% or more identity with SEQ ID NO: 6. More preferably, the isolated or purified polypeptide molecule shares 30% or more identity with SEQ ID NO: 6. Still more preferably, the isolated or purified polypeptide molecule shares 45% or more identity with SEQ ID NO: 6. Even more preferably, the isolated or purified polypeptide molecule shares 65% or more identity with SEQ ID NO: 6.

An isolated or purified polypeptide molecule consisting essentially of an amino acid sequence encoding a variant TDC1 or a fragment thereof can comprise at least 95 contiguous amino acids, which is optionally glycosylated, amidated, carboxylated, phosphorylated, esterified, N-acylated or converted into an acid addition salt. Still preferably, the fragment comprises at least 100 contiguous amino acids. Still more preferably, the fragment comprises at least 105 contiguous amino acids. Even more preferably, the fragment comprises at least 10 contiguous amino acids.

The present invention further provides an isolated or purified polypeptide molecule consisting essentially of an amino acid sequence encoding TDC2 or a fragment thereof comprising at least 71 contiguous amino acids, either one of which is optionally glycosylated, amidated, carboxylated, phosphorylated, esterified, N-acylated or converted into an acid addition salt. The isolated or purified polypeptide molecule is preferably obtained from a mammalian source. Even more preferably, the mammalian source is a human. The isolated or purified polypeptide molecule can be encoded by the nucleotide sequence of SEQ ID NO: 3 or a fragment thereof comprising at least 213 contiguous nucleotides. Preferably, the isolated or purified polypeptide molecule consists essentially of the amino acid sequence of SEQ ID NO: 4 or a fragment thereof comprising at least 71 contiguous amino acids. More preferably, the fragment comprises at least 75 contiguous amino acids. Still more preferably, the fragment comprises at least 90 contiguous amino acids. Even more preferably, the fragment comprises at least 105 contiguous amino acids. Alternatively, but still preferably, the isolated or purified polypeptide molecule shares 31% or more identity with SEQ ID NO: 4. More preferably, the isolated or purified polypeptide molecule shares 40% or more identity with SEQ ID NO: 4. Still more preferably, the isolated or purified polypeptide molecule shares 55% or more identity with SEQ ID NO: 4. Even more preferably, the isolated or purified polypeptide molecule shares 75% or more identity with SEQ ID NO: 4.

In a further embodiment, the isolated or purified polypeptide molecule can be encoded by the nucleotide sequence of SEQ ID NO: 7 or a fragment thereof comprising at least 213 contiguous nucleotides. Preferably, the isolated or purified polypeptide molecule consists essentially of the amino acid sequence of SEQ ID NO: 8 or a fragment thereof comprising at least 71 contiguous amino acids. More preferably, the fragment comprises at least 75 contiguous amino acids. Still more preferably, the fragment comprises at least 90 contiguous amino acids. Even more preferably, the fragment comprises at least 105 contiguous amino acids. Alternatively, but still preferably, the isolated or purified polypeptide molecule shares 34% or more identity with SEQ ID NO: 8. More preferably, the isolated or purified polypeptide molecule shares 40% or more identity with SEQ ID NO: 8. Still more preferably, the isolated or purified polypeptide molecule shares 55% or more identity with SEQ ID NO: 8. Even more preferably, the isolated or purified polypeptide molecule shares 75% or more identity with SEQ ID NO: 8.

An isolated or purified polypeptide molecule consisting essentially of an amino acid sequence encoding a variant TDC2 or a fragment thereof can comprise at least 71 contiguous amino acids, which is optionally glycosylated, amidated, carboxylated, phosphorylated, esterified, N-acylated or converted into an acid addition salt. Still preferably, the fragment comprises at least 75 contiguous amino acids. Still more preferably, the fragment comprises at least 90 contiguous amino acids. Even more preferably, the fragment comprises at least 115 contiguous amino acids.

The polypeptide preferably comprises an amino end and a carboxyl end. The polypeptide can comprise D-amino acids, L-amino acids or a mixture of D- and L-amino acids. The D-form of the amino acids, however, is particularly preferred since a polypeptide comprised of D-amino acids is expected to have a greater retention of its biological activity in vivo, given that the D-amino acids are not recognized by naturally occurring proteases.

The polypeptide can be prepared by any of a number of conventional techniques. The polypeptide can be isolated or purified from a naturally occurring source or from a recombinant source. For instance, in the case of recombinant polypeptides, a DNA fragment encoding a desired peptide can be subcloned into an appropriate vector using well-known molecular genetic techniques (see, e.g., Maniatis et al., *Molecular Cloning: A Laboratory Manual*, 2nd ed. (Cold Spring Harbor Laboratory, 1989); and Sambrook et al., Molecular Cloning: A Laboratory Manual, 2nd ed. Cold Spring Harbor Press, Cold Spring Harbor, N.Y., 1989). The fragment can be transcribed and the polypeptide subsequently translated in vitro. Commercially available kits can also be employed (e.g., such as manufactured by Clontech, Palo Alto, Calif.; Amersham Life Sciences, Inc., Arlington Heights, Ill., InVitrogen, San Diego, Calif., and the like). The polymerase chain reaction optionally can be employed in the manipulation of nucleic acids. In addition, the polypeptide or fragment thereof can be glycosylated in accordance with methods known in the art.

Alterations of the native amino acid sequence to produce variant polypeptides can be done by a variety of means known to those skilled in the art. For instance, site-specific mutations can be introduced by ligating into an expression vector a synthesized oligonucleotide comprising the modified site. Alternately, oligonucleotide-directed site-specific mutagenesis procedures can be used such as disclosed in Walder et al., *Gene*, 42, 133 (1986); Bauer et al., *Gene*, 37, 73 (1985); Craik, *Biotechniques*, 12-19 (January 1995); and U.S. Pat. Nos. 4,518,584 and 4,737,462.

With respect to the above isolated or purified polypeptides, one of ordinary skill in the art will appreciate that insertions, deletions, inversions and/or substitutions in a nucleotide sequence coding for functional domains of the transductin molecule can lead to a non-functional transductin molecule. Preferably, any variants, as described above, would contain mutations such as insertions, deletions, inversions and/or substitutions in domains which are not critical for transductin activity. For example, as an integral membrane protein, an insertion, inversion, deletion and/or substitution to the transmembrane domain of the transductin molecule may render the molecule unable to insert into the membrane, thus rendering it ineffective as a channel through the cell membrane. Alternatively, the mutation as described above may affect the ability of the channel pore domain to move molecules across the cell membrane. Other domains which are critical for transductin activity can be identified by determining if a mutation(s) to those domains causes a decrease in transductin activity.

Any appropriate expression vector (e.g., as described in Pouwels et al., *Cloning Vectors: A Laboratory Manual* (Elsevier, N.Y.: 1985)) and corresponding suitable host can be employed for production of recombinant polypeptides. Expression hosts include, but are not limited to, bacterial species within the genera *Escherichia, Bacillus, Pseudomonas, Salmonella*, mammalian or insect host cell systems including baculovirus systems (e.g., as described by Luckow et al., *Bio/Technology*, 6, 47 (1988)), and established cell lines such as the COS-7, C127, 3T3, CHO, HeLa, BHK cell line, and the like. The ordinary skilled artisan is, of course, aware that the choice of expression host has ramifications for the type of polypeptide produced. For instance the glycosylation of polypeptides produced in yeast or mammalian cells (e.g., COS-7 cells) will differ from that of polypeptides produced in bacterial cells such as *Escherichia coli*.

Alternately, the polypeptide (including the variant peptides) can be synthesized using standard peptide synthesizing techniques well-known to those of skill in the art (e.g., as summarized in Bodanszky, *Principles of Peptide Synthesis*, (Springer-Verlag, Heidelberg: 1984)). In particular, the polypeptide can be synthesized using the procedure of solid-phase synthesis (see, e.g., Merrifield, *J. Am. Chem. Soc.*, 85, 2149-54 (1963); Barany et al., *Int. J. Peptide Protein Res.*, 30 705-739 (1987); and U.S. Pat. No. 5,424,398). If desired, this can be done using an automated peptide synthesizer. Removal of the t-butyloxycarbonyl (t-BOC) or 9-fluorenylmethyloxycarbonyl (Fmoc) amino acid blocking groups and separation of the polypeptide from the resin can be accomplished by, for example, acid treatment at reduced temperature. The polypeptide-containing mixture can then be extracted, for instance, with dimethyl ether, to remove non-peptidic organic compounds, and the synthesized polypeptide can be extracted from the resin powder (e.g., with about 25% w/v acetic acid). Following the synthesis of the polypeptide, further purification (e.g., using high performance liquid chromatography (HPLC)) optionally can be done in order to eliminate any incomplete polypeptides or free amino acids. Amino acid and/or HPLC analysis can be performed on the synthesized polypeptide to validate its identity. For other applications according to the invention, it may be preferable to produce the polypeptide as part of a larger fusion protein, either by chemical conjugation, or through genetic means, such as are known to those skilled in the art.

If desired, the polypeptides of the invention (including variant polypeptides) can be modified, for instance, by glycosylation, amidation, carboxylation, or phosphorylation, or by the creation of acid addition salts, amides, esters, in particular C-terminal esters, and N-acyl derivatives of the polypeptides of the invention. The polypeptides also can be modified to create polypeptide derivatives by forming covalent or noncovalent complexes with other moieties in accordance with methods known in the art. Covalently-bound complexes can be prepared by linking the chemical moieties to functional groups on the side chains of amino acids comprising the polypeptides, or at the N- or C-terminus.

Thus, in this regard, the present invention also provides a conjugate comprising an above-described isolated or purified polypeptide molecule or fragment thereof and a targeting moiety. Preferably, the targeting moiety is an antibody or an antigenically reactive fragment thereof. Alternatively, the targeting moiety can be a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). Methods of conjugation are known in the art. In addition, conjugate kits are commercially available.

The present invention also provides a composition comprising a pharmaceutically acceptable carrier and either (i) an above-described isolated or purified nucleic acid molecule or fragment thereof, (ii) an above-described vector, (iii) an above-described polypeptide molecule or fragment thereof, or (iv) an above-described conjugate comprising an above-described isolated or purified polypeptide molecule or fragment thereof and a targeting moiety. Pharmaceutically acceptable carriers are well-known in the art, and are readily available. The choice of carrier will be determined in part by the particular route of administration and whether a nucleic acid molecule or a polypeptide molecule (or conjugate thereof) is being administered. Accordingly, there is a wide variety of suitable formulations for use in the context of the present invention, and the invention expressly provide a pharmaceutical composition that comprises an active agent of the invention and a pharmaceutically acceptable carrier therefor. The following methods and carriers are merely exemplary and are in no way limiting.

Formulations suitable for oral administration can consist of (a) liquid solutions, such as an effective amount of the compound dissolved in diluent, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth. Pastilles can comprise the active ingredient in an inert base, such as gelatin and glycerin, or sucrose and acacia, emulsions, gels, and the like containing, in addition to the active ingredient, such excipients/carriers as are known in the art.

An active agent of the present invention, either alone or in combination with other suitable components, can be made into aerosol formulations to be administered via inhalation. These aerosol formulations can be placed into pressurized acceptable propellants, such as dichlorodifluoromethane, propane, nitrogen, and the like. They also can be formulated as pharmaceuticals for non-pressured preparations such as in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, active agents of the present invention can be made into suppositories by mixing with a variety of bases such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate. Further suitable formulations are found in *Remington's Pharmaceutical Sciences*, 17th ed., (Mack Publishing Company, Philadelphia, Pa.: 1985), and methods of drug delivery are reviewed in, for example, Langer, *Science*, 249, 1527-1533 (1990).

A targeting moiety also can be used in the contact of a cell with an above-described isolated or purified nucleic acid molecule. In this regard, any molecule that can be linked with the therapeutic nucleic acid directly or indirectly, such as through a suitable delivery vehicle, such that the targeting moiety binds to a cell-surface receptor, can be used. The targeting moiety can bind to a cell through a receptor, a substrate, an antigenic determinant or another binding site on the surface of the cell. Examples of a targeting moiety include an antibody (i.e., a polyclonal or a monoclonal antibody), an immunologically reactive fragment of an antibody, an engineered immunoprotein and the like, a protein (target is receptor, as substrate, or regulatory site on DNA or RNA), a polypeptide (target is receptor), a peptide (target is receptor), a nucleic acid, which is DNA or RNA (i.e., single-stranded or double-stranded, synthetic or isolated and purified from nature; target is complementary nucleic acid), a steroid (target is steroid receptor), and the like.

Analogs of targeting moieties that retain the ability to bind to a defined target also can be used. In addition, synthetic targeting moieties can be designed, such as to fit a particular epitope. Alternatively, the therapeutic nucleic acid can be encapsulated in a liposome comprising on its surface the targeting moiety.

The targeting moiety includes any linking group that can be used to join a targeting moiety to, in the context of the present invention, an above-described nucleic acid molecule, It will be evident to one skilled in the art that a variety of linking groups, including bifunctional reagents, can be used. The targeting moiety can be linked to the therapeutic nucleic acid by covalent or non-covalent bonding. If bonding is non-covalent, the conjugation can be through hydrogen bonding, ionic bonding, hydrophobic or van der Waals interactions, or any other appropriate type of binding.

Further provided by the present invention is a cell line that produces a monoclonal antibody that is specific for an above-described isolated or purified polypeptide molecule. Methods of making such cell lines are known in the art (see, e.g., the references cited herein under "Examples."). Preferably, the cells from which the cell line is created are pluripotent stem cells. Even more preferably, the cells are totipotent stem cells. Thus, the present invention also provides the monoclonal antibody produced by the cell line.

The invention further provides methods for detecting hearing loss or a predisposition to hearing loss in an animal. In one embodiment, the method comprises detecting at least one mutation such as 1714G→A (D572N), 100C→T (R34X), 1534C→T (R512X), 295 del A (frameshift and premature termination), 1960 A→G (M654V), IVS3$_{13}$ IVS5del27kb, IVS13+1G→A, or IVS10-8T→A, in a gene encoding TDC1 in a test sample comprising a nucleic acid comprising the TDC1 gene, and/or a polymorphism thereof obtained from the animal, wherein the at least one mutation is indicative of hearing loss or a predisposition to hearing loss in the animal. In another embodiment, the method comprises detecting at least one mutation in a gene encoding TDC2 in a test sample comprising a nucleic acid comprising the TDC2 gene, and/or a polymorphism thereof, obtained from the animal, wherein the at least one mutation is indicative of hearing loss or a predisposition to hearing loss in the animal. The hearing loss can be hereditary, and can further be sensorineural hearing loss. The method can further be used to treat nonsyndromic autosomal-dominant hearing loss. The hearing loss can also be aminoglycoside induced. Furthermore, the hearing loss can be linked to DFNA 36. The method also has application wherein the at least one mutation compromises the ability of the TDC1/TDC2 gene product to form a component of a hair cell of the inner ear of the animal. The component of the hair cell can be all or some of an ion transduction channel of the hair cell of the inner ear of the animal. Alternatively, the at least one mutation can compromise the mechanosensory activity of the TDC1/TDC2 gene product.

The at least one mutation (e.g., at least two mutations, at least three mutations, at least four mutations, at least five mutations, or even at least ten mutations) in a gene encoding transductin is defined herein as any one or more mutations in the gene encoding transductin which is/are indicative of hearing loss or a predisposition to hearing loss in an animal. The at least one mutation can be, for example, any frame-shift mutations, missense mutations and/or nonsense mutations, arising from any insertion, duplication, deletion, inversion, and/or substitution in a gene encoding transductin. The at least one mutation can cause transcriptional, post-transcriptional, translational, and/or post-translational processing errors, e.g., a translation error wherein translation begins at a codon encoding a methionine other than the first methionine of the transductin gene (e.g., a codon encoding the third methionine of the transductin gene). Moreover, the at least one mutation in the transductin gene can cause one or more splicing errors (i.e., splicing mutations), such that a mutant transductin gene is produced. Alternatively, or in addition to, the at least one mutation in the transductin gene can be a mutation that causes transcriptional, post-transcriptional, translational, and/or post-transcriptional processing of the transductin gene to stop prematurely, thereby leading to the expression of a truncated form of transductin. The at least one mutation can also cause a decreased efficiency of transcriptional, post-transcriptional, translational, and/or post-translational processing of the transductin gene product. Moreover, the at least one mutation in the transductin gene can be associated with a compromised ability of the transductin gene product to function normally, as compared to wild-type transductin.

The at least one mutation in the transductin gene can be detected at one or more nucleic acid positions of the transductin gene, e.g., within any coding region, and/or regulatory region of the transductin gene. The at least one mutation in the transductin gene is indicative of hearing loss or a predisposition to hearing loss in the animal if, for example, the at least one mutation compromises the transmembrane domain allowing the transductin molecule to traverse the cell membrane. The at least one mutation in the transductin gene also is indicative of hearing loss or a predisposition to hearing loss in an animal if it compromises the ability of the transductin molecule from associating with other such molecules to form an ion channel. Moreover, the at least one mutation in the transductin gene is indicative of hearing loss or a predisposition to hearing loss in an animal if the at least one mutation compromises the ability of the transductin gene product to become activated, as compared to wild-type transductin; or compromises the ability of the channel complex to channel ions across a cell membrane.

The transductin gene in a test sample obtained from an animal can be amplified using any suitable amplification method known in the art, e.g., polymerase chain reaction (PCR); reverse transcriptase PCR (RT-PCR); ligase chain reaction (LCR) (disclosed in U.S. Pat. No. 4,883,750); isothermal amplification (disclosed in Walker et al., *Proc. Natl Acad. Sci. USA* 89: 392-396 (1992)); strand displacement amplification (SDA); and repair chain reaction (RCR). Target-specific sequences also can be detected using a cyclic probe reaction (CPR). Moreover, alternative methods for reverse transcription are described in WO 90/07641.

Any primer sequences can be used in the amplification process, as long as the primer sequences are hybridizable to nucleic acids encoding a wild-type transductin gene, a mutant transductin gene, and/or functional sequence analogs thereof. For example, M13-tailed primers can be used in the amplification process (see Table 1).

The nucleic acid used as a template for amplification can be isolated from a test sample using any standard methodology (Sambrook et al., Molecular Cloning: A Laboratory Manual, 2$^{nd}$Ed., Cold Spring Harbor Press, Cold Spring Harbor, N.Y., 1989). Alternatively, or in addition to, chromatographic techniques can be employed to effect separation. It will be understood that there are many kinds of chromatography which can be used in the context of the method, e.g., adsorption, partition, ion-exchange and molecular sieve, and many specialized techniques for using them including column, paper, thin-layer and gas chromatography (Freifelder, *Physical Biochemistry Applications to Biochemistry and Molecular Biology*, 2$^{nd}$ Ed., Wm. Freeman and Co., New York, N.Y. (1982)).

Amplification products must be visualized in order to confirm amplification of the transductin gene. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation. In one embodiment, visualization is achieved indirectly. Following separation of amplification products, a labeled, nucleic acid probe is brought into contact with and allowed to hybridize with the amplified transductin gene sequence. The probe preferably is conjugated to a chromophore, but may be radiolabeled. In another embodiment, the probe is conjugated to a binding partner, such as an antibody or biotin, where the other member of the binding pair carries a detectable moiety (i.e., a label). One example of the foregoing is described in U.S. Pat. No. 5,279,721, which discloses an apparatus and method for the automated electrophoresis and transfer of nucleic acids.

When hybridization is employed, preferably, the hybridization is done under high stringency conditions. By "high stringency conditions" is meant that the probe specifically hybridizes to a target sequence in an amount that is detectably stronger than non-specific hybridization. High stringency conditions, then, are conditions that distinguish a polynucleotide with an exact complementary sequence, or one containing only a few scattered mismatches from a random sequence that happened to have a few small regions (e.g., 3-10 bases) that matched the probe. Such small regions of complementarity are more easily melted than a full-length complement of 14-17 or more bases, and moderate stringency hybridization makes them easily distinguishable. Relatively high stringency conditions include, for example, low salt and/or high temperature conditions, such as provided by about 0.02-0,1 M NaCl or the equivalent, at temperatures of about 50-70° C. Such relatively high stringency conditions tolerate little, if any, mismatch between the probe and the template or target strand, and are particularly suitable for detecting expression of specific transductins. It is generally appreciated that conditions can be rendered more stringent by the addition of increasing amounts of formamide.

The at least one mutation can be detected by sequencing the transductin gene, and comparing the sequence to the wild-type sequence. Alternatively, the at least one mutation may be detected by Southern blot hybridization, a method well known in the art. Yet another alternative is by allele-specific PCR amplification of genomic DNA.

In addition to the above, the invention provides a method of determining the level of nucleic acid comprising the wild-type TDC1 gene and/or a mutant TDC1 gene in a test sample comprising a nucleic acid comprising the wild-type TDC1 gene and/or a mutant TDC1 gene obtained from an animal. The method comprises assaying the test sample for the level of nucleic acid comprising the wild-type TDC1 gene and/or a mutant TDC1 gene, wherein a decrease in the level of nucleic acid comprising the wild-type TDC1 gene and/or an increase in the level of nucleic acid comprising a mutant TDC1 gene in the test sample as compared to a control sample is indicative of hearing loss (e.g., hearing loss) or a predisposition to hearing loss in the animal.

In addition to the above, the invention provides a method of determining the level of nucleic acid comprising the wild-type TDC2 gene and/or a mutant TDC2 gene in a test sample comprising a nucleic acid comprising the wild-type TDC2 gene and/or a mutant TDC2 gene obtained from an animal. The method comprises assaying the test sample for the level of nucleic acid comprising the wild-type TDC2 gene and/or a mutant TDC2 gene, wherein a decrease in the level of nucleic acid comprising the wild-type TDC2 gene and/or an increase in the level of nucleic acid comprising a mutant TDC2 gene in the test sample as compared to a control sample is indicative of hearing loss (e.g., hearing loss) or a predisposition to hearing loss in the animal.

A wild-type transductin gene is defined herein is any transductin gene that encodes an transductin gene product that has (i.e., possesses) cation channel capabilities across a cell membrane. A mutant transductin gene is defined herein as any transductin gene that encodes a transductin gene product which has a compromised ability (e.g., little or no ability) to channel cations across a cell membrane, as compared to wild-type transductin.

The level of a wild-type transductin gene and/or a mutant transductin gene in a test sample obtained from an animal is defined herein as the quantity of nucleic acid comprising a wild-type transductin gene and/or the quantity of nucleic acid comprising a mutant transductin gene in the test sample. "Decreased" and "increased" levels of the wild-type transductin gene and/or a mutant transductin gene are determined by a comparison of the level of wild-type and/or mutant transductin genes present in a test sample obtained from an animal to any suitable control test sample. Suitable control test samples include, for example, a test sample obtained from the same animal at a different point in time and a test sample obtained from a different animal of the same species.

Various assays can be used to measure the presence and/or level of nucleic acid (i.e., DNA or RNA) comprising a wild-type transductin gene and/or a mutant transductin gene present in a test sample obtained from an animal. For example, assays including PCR and microarray analysis can be used to detect the presence and/or absence of the wild-type transductin gene and/or a mutant transductin gene, as described, for example, in U.S. Pat. Nos. 6,197,506 and 6,040,138. Moreover, it is understood that the type of assay used depends on whether the nucleic acid of interest being assayed is DNA or RNA. Assays for determining the level of DNA comprising a wild-type transductin gene and/or a mutant transductin gene in a test sample include, for example, Southern hybridization (i.e., a Southern blot), in situ hybridization and microarray analysis. Assays for determining the level of RNA (e.g., mRNA) comprising a wild-type transductin gene and/or a mutant transductin gene in a test sample include, for example, Northern hybridization (i.e., a Northern blot), in situ hybridization and microarray analysis.

It is also understood that a nucleic acid sequence that specifically binds to, or associates with, a nucleic acid comprising a gene encoding transductin, whether DNA or RNA, can be attached to a label for determining hybridization. A wide variety of appropriate labels are known in the art, including, for example, fluorescent, radioactive, and enzymatic labels, as well as ligands (e.g., avidir/biotin), which are capable of being detected. Preferably, a fluorescent label or an enzyme tag, such as urease, alkaline phosphatase or peroxidase, is used instead of a radioactive or other environmentally undesirable label. In the case of enzyme tags, calorimetric indicator substrates are known which can be employed to provide a detection system that is visible spectrophotometrically, or even visible to the human eye to identify specific hybridization with complementary transductin nucleic acid-containing samples.

The invention also provides for the use of the method in prognosticating hearing loss (e.g., hearing loss) in an animal. The method comprises determining the level of nucleic acid comprising the wild-type TDC1/TDC2 gene and/or a mutant TDC1/TDC2 gene in a test sample comprising a nucleic acid comprising the wild-type TDC1/TDC2 gene and/or a mutant TDC1/TDC2 gene obtained from the animal, and comparing the level of nucleic acid comprising the wild-type TDC1/TDC2 gene and/or a mutant TDC1/TDC2 gene in the test sample to the level of nucleic acid comprising the wild-type TDC1/TDC2 gene and/or a mutant TDC1/TDC2 gene, respectively, in another test sample obtained from the animal over time, wherein a decrease in the level of nucleic acid comprising the wild-type TDC1/TDC2 gene and/or an increase in the level of nucleic acid comprising a mutant TDC1/TDC2 gene is indicative of an unfavorable prognosis, an increase in the level of the nucleic acid comprising the wild-type TDC1/TDC2 gene and/or a decrease in the level of the nucleic acid comprising a mutant TDC1/TDC2 gene is indicative of a favorable prognosis, and no change in the level of nucleic acid comprising the wild-type TDC1/TDC2 gene and/or a mutant TDC1/TDC2 gene is indicative of no change in the hearing loss.

The invention also provides for the use of the method in assessing the efficacy of treatment of hearing loss in the animal with a given anti-hearing loss agent. The method comprises comparing the level of nucleic acid comprising the wild-type TDC1/TDC2 gene and/or a mutant TDC1/TDC2 gene in the test sample to the level of nucleic acid comprising the wild-type TDC1/TDC2 gene and/or a mutant TDC1/TDC2 gene, respectively, in another test sample obtained from the animal over time, wherein a decrease in the level of nucleic acid comprising the wild-type TDC1/TDC2 gene and/or an increase in the level of nucleic acid comprising a mutant TDC1/TDC2 gene is indicative of the anti-hearing loss agent being effective, an increase in the level of the nucleic acid comprising the wild-type TDC1/TDC2 gene and/or a decrease in the level of the nucleic acid comprising a mutant TDC1/TDC2 gene is indicative of the anti-hearing loss agent being ineffective, and no change in the level of nucleic acid comprising the wild-type TDC1/TDC2 gene and/or a mutant TDC1/TDC2 gene is indicative of no change in the hearing loss due to treatment with the anti-hearing loss agent.

A mutant transductin gene product also can be detected in a test sample obtained from an animal and is indicative of hearing loss or a predisposition to hearing loss in the animal. Accordingly, the present invention further provides a method for detecting hearing loss or a predisposition to hearing loss in an animal comprising detecting a mutant transductin in a test sample comprising protein comprising transductin obtained from the animal, wherein the presence of a mutant transductin in the test sample is indicative of hearing loss or a predisposition to hearing loss in the animal. Examples of such mutations, which are indicative of hearing loss or a predisposition to hearing loss, have been described above. Thus, the method comprises detecting a mutant TDC1/TDC2 in a test sample comprising protein comprising TDC1/TDC2 obtained from the animal, wherein the presence of a mutant TDC1/TDC2 in the sample is indicative of hearing loss, or a predisposition to hearing loss in the animal. The hearing loss can be hereditary, sensorineural hearing loss, nonsyndromic autosomal-dominant, and/or DFNA 36-linked hearing loss. The ability of the mutant TDC1/TDC2 to form a component of a hair cell of the inner ear of the animal can be compromised. The ability of the mutant TDC1/TDC2 to form all or some of an on transduction channel of the hair cell of the inner ear of the animal can be compromised. The mechanosensory activity of the mutant TDC1/TDC2 can also be compromised.

The levels of wild-type TDC1/TDC2 and/or a mutant TDC1/TDC2 also can be determined. Accordingly, the invention also provides a method of determining the level of wild-type TDC1/TDC2 and/or a mutant TDC1/TDC2 in a test sample comprising protein comprising wild-type TDC1/TDC2 and/or a mutant TDC1/TDC2 obtained from an animal. The method comprises assaying the test sample for the level of wild-type TDC1/TDC2 and/or a mutant TDC1/TDC2, wherein a decrease in the level of wild-type TDC1/TDC2 and/or an increase in the level of a mutant TDC1/TDC2 in the test sample as compared to a control sample (as described previously) is indicative of hearing loss or a predisposition to hearing loss in the animal.

Various assays (i.e., immunobinding assays) are contemplated for detecting and/or measuring the quantity of wild-type transductin and/or a mutant transductin in a test sample obtained from an animal. For example, separate and distinct antibodies can be prepared and employed to detect wild-type transductin and a mutant transductin, respectively. Alternatively, wild-type transductin and a mutant transductin can be utilized to detect antibodies having reactivity therewith. The steps of various useful immunodetection assays have been described, for example, in Nakamura et al., *Handbook of Experimental Immunology* (4$^{th}$ Ed)., Vol. 1, Chapter 27, Blackwell Scientific Publ., Oxford (1987); Nakamura et al., *Enzyme Immunoassays: Heterogenous and Homogenous Systems*, Chapter 27 (1987). Suitable immunoassays include, for example, Western hybridization (i.e., Western blots), immunoaffinity purification, immunoaffinity detection, enzyme-linked immunosorbent assay (e.g., an ELISA), and radioimmunoassay. Moreover, a microarray can be used to detect and/or measure the levels of wild-type transductin and/or a mutant transductin in a test sample obtained from an animal.

In general, the immunobinding assays involve obtaining a test sample suspected of containing a protein, peptide, polypeptide, and/or antibody corresponding to wild-type transductin and/or a mutant transductin, and contacting the test sample with one or more antibodies under conditions effective to allow the formation of immunocomplexes. It is suitable, for example, to contact concurrently, or sequentially, a test sample obtained from an animal with an antibody that is specific to wild-type transductin and with an antibody that is specific to a mutant transductin.

Any suitable antibody can be used in conjunction with the present invention such that the antibody is specific for wild-type transductin. Likewise, any suitable antibody can be used in conjunction with the present invention such that the antibody is specific for a mutant transductin. In particular, suitable antibodies recognize and interact with (i.e., bind to) one or more portions of wild-type transductin and with one or more portions of a mutant transductin. Moreover, suitable antibodies include antibodies that recognize and interact with other antibodies present in a test sample that bind to wild-type transductin. Likewise, suitable antibodies include antibodies that recognize and interact with other antibodies present in a test sample that bind to a mutant transductin. Antibodies for use in the present inventive methods can be produced by any known technique, e.g., as described in Antibodies: A Laboratory Manual, Cold Spring Harbor Laboratory (1988).

Contacting a test sample comprising a protein comprising wild-type transductin and/or a mutant transductin with an antibody or antibodies that recognize wild-type transductin and/or a mutant transductin under conditions effective, and for a period of time sufficient, to allow for formation of immune complexes (primary immune complexes) is generally a matter of adding the antibody to the test sample and incubating the mixture for a period of time long enough for the antibodies to form immune complexes with wild-type transductin and/or a mutant transductin. Detection of immunocomplex formations can be achieved through the application of numerous techniques which are well-known in the art. These detection methods are generally based upon the detection of a label or marker, such as any radioactive, fluorescent, biological a enzymatic labels of standard use in the art, as described, for example, in U.S. Pat. Nos. 3,817,837, 3,850, 752, 3,939,350, 3,996,345, 4,277,437, 4,275,149 and 4,366, 241. Of course, additional advantages can be realized by using a secondary binding ligand, such as a second antibody or a biotin/avidin ligand binding arrangement, as is known in the art.

The antibody or antibodies which is/are used in the context of the present invention can, themselves, be linked to a detectable label. Such a detectable label allows for the presence of, or the amount of, the primary immune complexes to be determined. Alternatively, the first added component that becomes bound within the primary immune complexes can be detected by means of a second binding ligand that has binding affinity for the first antibody. In these cases, the second binding ligand is, itself, often an antibody, which can be termed a "secondary" antibody. The primary immune complexes are contacted with the labeled, secondary binding ligand, or antibody, under conditions effective and for a period of time sufficient to allow the formation of secondary immune complexes. The secondary immune complexes are then washed to remove any non-specifically bound labeled secondary antibodies or ligands, and the remaining label in the secondary immune complexes is then detected.

Further methods include the detection of primary immune complexes by a two-step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed.

The invention also provides for the use of the method in prognosticating hearing loss in an animal. The method comprises comparing the level of wild-type TDC1/TDC2 and/or a mutant TDC1/TDC2 in the test sample to the level of wild-type TDC1/TDC2 and/or a mutant TDC1/TDC2, respectively, in another test sample obtained from the animal over time, wherein a decrease in the level of wild-type TDC1/TDC2 and/or an increase in the level of a mutant TDC1/TDC2 is indicative of an unfavorable prognosis, an increase in the level of the wild-type TDC1/TDC2 and/or a decrease in the level of a mutant TDC1/TDC2 is indicative of a favorable prognosis, and no change in the level of the wild-type TDC1/TDC2 and/or a mutant TDC1/TDC2 gene is indicative of no change in the hearing loss.

The invention also provides for the use of the method in assessing the efficacy of treatment of hearing loss in an animal. The method comprises comparing the level of wild-type TDC1/TDC2 and/or a mutant TDC1/TDC2 in the test sample to the level of wild-type TDC1/TDC2 and/or a mutant TDC1/ TDC2, respectively, in another test sample obtained from the animal over time, wherein a decrease in the level of the wild-type TDC1/TDC2 and/or an increase in the level of a mutant TDC1/TDC2 is indicative of the anti-hearing loss agent being effective, an increase in the level of the wild-type TDC1/TDC2 and/or a decrease in the level of a mutant TDC1/ TDC2 is indicative of the anti-hearing loss agent being ineffective, and no change in the level of the wild-type TDC1/ TDC2 and/or a mutant TDC1/TDC2 is indicative of no change in the hearing loss due to treatment with the anti-hearing loss agent.

The invention also provides a method of treating an animal prophylactically or therapeutically for hearing loss (e.g., hearing loss), wherein the hearing loss is due to a complete or partial loss of wild-type TDC1/TDC2, which method comprises providing TDC1/TDC2 to the animal, whereupon the animal is treated prophylactically or therapeutically for hearing loss. Use of the terms "prophylactically," "prophylaxis," and derivatives of these terms is not meant to be limited to absolute prevention of hearing loss, but also less than 100% prevention of hearing loss. The ordinarily skilled artisan will appreciate that a less than 100% prevention of hearing loss may still be beneficial to an animal, and thus contemplated to be within the scope of the present invention. The hearing loss can be hereditary, sensorineural hearing loss, nonsyndromic autosomal-dominant, and/or DFNA 36-linked hearing loss. The ability of the mutant TDC1/TDC2 to form a component of a hair cell of the inner ear of the animal can be compromised. The ability of the mutant TDC1/TDC2 to form all or some of an on transduction channel of the hair cell of the inner ear of the animal can be compromised. The mechanosensory activity of the mutant TDC1/TDC2 also can be compromised.

Any suitable method can be used for administering or providing transductin to an animal, wherein the transductin enters the nucleus and/or cytoplasm of one or more hearing loss cells (e.g., one or more hearing loss cells) of the animal and functions within the cell(s) in a manner which is typical of wild-type transductin. For example, transductin can be provided to the animal by administering to the animal the wild-type transductin protein, or a portion thereof (e.g., two or more different forms of wild-type transductin). Moreover, transductin can be provided to an animal through administration of a fusion protein comprising wild-type transductin, or a portion thereof, operably linked to one or more moieties of interest (e.g., two or more, three or more, four or more, or five or more therapeutic moieties, such as anti-hearing loss agents, and/or any compounds which stimulate transductin). In another embodiment, transductin is provided to an animal through administration of a nucleic acid encoding and expressing wild-type transduction, or a portion thereof. Moreover, transductin can be provided to an animal through administration of a nucleic acid encoding and expressing a fusion protein comprising wild-type transduction, or a portion thereof, operably linked to one or more moieties of interest. The administered nucleic acid can be in any suitable form. For example, the administered nucleic acid can be naked DNA or RNA. Moreover, the administered nucleic acid can be part of any suitable vector or vector system. Suitable vectors for use in the method include, for example, plasmid vectors, retroviral vectors, adenoviral vectors, adeno-associated viral vectors, vaccinia virus, sindbis virus, cytomegalovirus, herpes simplex virus, defective hepatitis B viruses, and any other vector or vector system known in the art. Fusion proteins and nucleic acids encoding and expressing fusion proteins can be produced using any standard methods of recombinant production and synthesis known in the art, as described, for example, in Sambrook et al., *Molecular Clon-*

*ing: A Laboratory Manual*, 2nd Ed., Cold Spring Harbor Press, Cold Spring Harbor, N.Y., 1989.

In view of the above, also provided is a composition. The composition comprises (i) a pharmaceutically acceptable carrier and (ii) transductin or a portion thereof; a fusion protein comprising transductin or a portion thereof operably linked to one or more moieties of interest; a nucleic acid encoding and expressing transduction or a portion thereof; and/or a nucleic acid encoding and expressing a fusion protein comprising transductin or a portion thereof, operably linked to one or more moieties of interest.

The carrier can be any suitable carrier. Preferably, the carrier is a pharmaceutically acceptable carrier. With respect to compositions, the carrier can be any of those conventionally used and is limited only by chemico-physical considerations, such as solubility and lack of reactivity with transductin, and by the route of administration. It will be appreciated by one of skill in the art that, in addition to the above-described composition, the compositions of the present inventive methods can be formulated as inclusion complexes, such as cyclodextrin inclusion complexes, or liposomes. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to transductin and one which has no detrimental side effects or toxicity under the conditions of use.

As is understood in the art, the choice of carrier is dependent on several factors, e.g., the type of hearing loss being treated and the route of administration of the composition. Such a choice of carrier for use in the composition of the present invention is well within the ordinary skill in the art. Accordingly, there are a variety of suitable formulations of the composition of the present invention. Such formulations include but, are not limited to, oral, aerosol, parenteral, subcutaneous, intravenous, intramuscular, interperitoneal, rectal, and vaginal formulations.

One skilled in the art will appreciate that suitable methods of administering a composition of the invention to an animal, in particular a human, are available, and, although more than one route can be used to administer a particular compound, a particular route can provide a more immediate and more effective reaction than another route.

Desirably, gene replacement therapy would be employed to treat therapeutically hereditary deafness in a mammal resulting from a mutation or deletion of TDC1 and/or TDC2. Methods of constructing vectors encoding therapeutic genes are known to one of ordinary skill in the art. Such constructs include viral vectors, preferably adenoviral or adeno-associated viral vectors, naked DNA, plasmid vector, and other genetic constructs. The vectors can be delivered by any method known in the art. Ideally, these vectors would be delivered to the animal transtympanically.

The dose administered to an animal, in particular a human, should be sufficient to treat the hearing loss prophylactically or therapeutically. One skilled in the art will recognize that dosage will depend upon a variety of factors including the strength of the particular composition employed, as well as the age, species, condition, and body weight of the animal. The size of the dose will also be determined by the route, timing, and frequency of administration as well as the existence, nature, and extent of any adverse side-effects that might accompany the administration of a particular composition and the desired physiological effect.

Suitable doses and dosage regimens can be determined by conventional range-finding techniques known to those of ordinary skill in the art. Generally, a composition is initially administered in smaller dosages, which are less than the optimum dose of the composition. Thereafter, the dosage is increased by small increments until the optimum effect under the circumstances is reached.

Also provided is a method of identifying one or more agent(s) which interact with a mechanotransduction channel of a cell of an animal. This method comprises administering one or more agent(s) to the mechanotransduction channel and assaying the mechanotransduction activity of the mechanotransduction channel, wherein an increase or decrease in the mechanotransduction activity of the mechanotransduction channel is indicative of an interaction between one or more agents and the mechanotransduction channel of the cell of the animal. Preferably, the cell used in the present method would be a hair cell of the inner ear of the animal.

The activity of the mechanotransduction can be measured by techniques known to one of ordinary skill in the art. For example, the channel of ions across a cell membrane to create a electropotential can be measured as generally described by Corey et al., Ionic basis of the receptor potential in a vertebrate hair cell, *Nature* 281: 675-77 (1979), and Hudspeth et al., Sensitivity, polarity, and conductance change in response of vertebrate hair cells to controlled mechanical stimuli, *Proc. Natl. Acad. Sci. USA* 74(6): 2407-11 (1977).

Further provided is a method of identifying one or more agent(s) which interact with a TDC1 gene and/or a TDC2 gene in a cell, comprising administering one or more agents to the cell comprising the TDC1 gene and/or the TDC2 gene and assaying the expression level of the TDC1 gene and/or the TDC2 gene by the cell as described herein, supra, wherein an increase or decrease in the expression level of the TDC1 gene and/or the TDC2 gene, as the terms have been described, supra, is indicative of an interaction between one or more agents and the TDC1 gene and/or the TDC2 gene in the cell.

The ordinarily skilled artisan will recognize that several methods of assaying the expression level of the TDC1 gene and/or the TDC2 gene exist. For example, mRNA can be quantified by a Northern blot analysis using a polynucleotide synthesized to hybridize to mRNA encoding TDC1 and/or TDC2. The polynucleotide can be attached to a probe, or can contain a radioisotope to facilitate detection of specific hybridization of mRNA encoding TDC1 and/or TDC2. Alternatively, the level of expression of the TDC1 gene and/or the TDC2 gene can also be assayed by quantifying the TDC1 and/or TDC2 polypeptide produced by the cell. For example, the cells to which the one or more agents have been administered can be contacted with a monoclonal antibody specific to TDC1 or TDC2. Antibody assays for protein are also well-known in the art as described, supra.

While the present invention is described above in the context of hearing loss, it is possible that the present invention has application in the context of balance. Indeed, the inner ear is known to comprise two systems: the auditory system, which is mainly used for audition, and the vestibular system, which functions in maintaining balance and equilibrium of the body. It has been described herein that when the auditory system (i.e., the cochlea) expresses mutant forms of either TDC1 and/or TDC2, hearing loss results. It is possible, therefore, that the vestibular system, which is responsible for linear and angular acceleration (i.e., balance), can express mutant forms of these genes as well; however, since the vestibular system controls balance as opposed to audition, it is likely that mutations and/or low expression levels of these genes in the vestibular system would result in abnormal balance or even a complete loss of balance. Thus, the methods of the invention, as they relate to TDC1 and TDC2, can be carried out with respect to hearing loss and, possibly, abnormal balance or a predisposition to abnormal balance as well.

EXAMPLE

The following example further illustrates the invention but, of course, should not be construed as in any way limiting its scope.

The following references, to the extent that they provide exemplary procedural or other details supplementary to those set forth herein, are specifically incorporated herein by reference:

Biiren et al., *Genome Analysis: A Laboratory Manual Series, Volume* 1, *Analyzing DNA*, Cold Spring Harbor Laboratory Press, Cold Spring Harbor, N.Y. (1997), Birren et al., *Genome Analysis: A Laboratory Manual Series, Volume* 2, *Detecting Genes*, Cold Spring Harbor Laboratory Press, Cold Spring Harbor, N.Y. (1998), Birren et al., *Genome Analysis: A Laboratory Manual Series, Volume* 3, *Cloning Systems*, Cold Spring Harbor Laboratory Press, Cold Spring Harbor, N.Y. (1999), Birren et al., *Genome Analysis: A Laboratory Manual Series, Volume* 4, *Mapping Genomes*, Cold Spring Harbor Laboratory Press, Cold Spring Harbor, N.Y. (1999), Harlow et al., *Antibodies: A Laboratory Manual*, Cold Spring Harbor Laboratory Press, Cold Spring Harbor, N.Y. (1988), Harlow et al., *Using Antibodies: A Laboratory Manual*, Cold Spring Harbor Laboratory Press, Cold Spring Harbor, N.Y. (1999), and Sambrook et al., *Molecular Cloning: A Laboratory Manual*, $2^{nd}$ edition, Cold Spring Harbor Laboratory Press, Cold Spring Harbor, N.Y. (1989).

Example 1

Mouse and human cochlear cells were lysed, and mRNA transcripts were purified from the cell lysate. Methods of cell lysis and subsequent mRNA purification are well-known in the art. The Human Genome Project database was analyzed for the sequences in the human genome that correlated highly with hearing loss in linkage studies. DNA primers were constructed from this information using techniques known in the art. These primers were employed in reverse transcriptase-polymerase chain reaction (RT-PCR) and 5'- and 3'-rapid amplification of cDNA ends (RACE) on the purified mRNA from cochlear cell lysates. Both methods are also well-known in the art. The resulting cDNA molecules were sequenced and identified as TDC1 and TDC2.

All of the references cited herein are hereby incorporated in their entireties by reference.

While this invention has been described with an emphasis upon preferred embodiments, it will be obvious to those of ordinary skill in the art that variations of the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. An isolated or purified nucleic acid molecule consisting of SEQ ID NO: 1.
2. An isolated or purified nucleic acid molecule consisting of a nucleotide sequence that is completely complementary to the full length of the nucleotide sequence of SEQ ID NO:1.
3. A vector comprising the isolated or purified nucleic acid molecule of claim 1.
4. A composition comprising the isolated or purified nucleic acid molecule of claim 1 and a carrier.
5. An isolated cell comprising the vector of claim 3.
6. A vector comprising the isolated or purified nucleic acid molecule of claim 2.
7. A composition comprising the isolated or purified nucleic acid molecule of claim 2 and a carrier.
8. An isolated cell comprising the vector of claim 6.

* * * * *

UNITED STATES PATENT AND TRADEMARK OFFICE
CERTIFICATE OF CORRECTION

PATENT NO. : 7,659,115 B2
APPLICATION NO. : 11/615250
DATED : February 9, 2010
INVENTOR(S) : Griffith et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 6 days.

Signed and Sealed this

Thirtieth Day of November, 2010

David J. Kappos
*Director of the United States Patent and Trademark Office*